(12) United States Patent
Gazit et al.

(10) Patent No.: US 8,197,553 B2
(45) Date of Patent: Jun. 12, 2012

(54) COMPOSITE SCAFFOLDS AND METHODS USING SAME FOR GENERATING COMPLEX TISSUE GRAFTS

(75) Inventors: Dan Gazit, Maccabim (IL); Abraham J. Domb, Efrat (IL); Gadi Turgeman, Jerusalem (IL); Gadi Pelled, Jerusalem (IL); Tony Azzam, Nazareth (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 66 days.

(21) Appl. No.: 12/285,107

(22) Filed: Sep. 29, 2008

(65) Prior Publication Data

US 2009/0035349 A1   Feb. 5, 2009

Related U.S. Application Data

(63) Continuation of application No. 10/476,064, filed as application No. PCT/IL02/00336 on Apr. 30, 2002, now abandoned.

(60) Provisional application No. 60/287,003, filed on Apr. 30, 2001.

(51) Int. Cl.
*A61F 2/02* (2006.01)

(52) U.S. Cl. ..................... 623/23.75

(58) Field of Classification Search .... 623/23.72–23.76; 424/93.1, 520; 435/373, 395–406
See application file for complete search history.

(56) References Cited

U.S. PATENT DOCUMENTS

| | | |
|---|---|---|
| 4,670,286 A | 6/1987 | Nyilas et al. |
| 5,486,359 A | 1/1996 | Caplan et al. |
| 5,948,429 A | 9/1999 | Bell et al. |
| 5,965,436 A | 10/1999 | Thiede et al. |
| 6,043,066 A | 3/2000 | Mangano et al. |
| 6,143,293 A | 11/2000 | Weiss et al. |
| 6,176,874 B1 | 1/2001 | Vacanti et al. |
| 6,365,149 B2 | 4/2002 | Vyakarnam et al. |
| 6,365,173 B1 | 4/2002 | Domb et al. |
| 6,368,356 B1 | 4/2002 | Zhong et al. |
| 6,387,367 B1 | 5/2002 | Davis-Sproul et al. |
| 6,596,296 B1 | 7/2003 | Nelson et al. |
| 2002/0142457 A1 | 10/2002 | Umezawa et al. |
| 2002/0169122 A1 | 11/2002 | Majumdar et al. |
| 2003/0068817 A1 | 4/2003 | Gazit et al. |
| 2004/0203146 A1 | 10/2004 | Gazit et al. |

(Continued)

FOREIGN PATENT DOCUMENTS

EP   0992517   12/2000

(Continued)

OTHER PUBLICATIONS

Office Action Dated Dec. 23, 2007 From the Israeli Patent Office Re.: Application No. 158622.

(Continued)

*Primary Examiner* — William H Matthews

(57) ABSTRACT

A composite scaffold for engineering a heterogeneous tissue is provided. The composite scaffold includes: (a) a first scaffold being capable of supporting formation of a first tissue type thereupon; and (b) a second scaffold being capable of supporting formation of a second tissue type thereupon; wherein the first scaffold and the second scaffold are arranged with respect to each other such that when the first scaffold supports the first tissue type and the second scaffold supports the second tissue type, a distance between any cell of the second tissue type and the first tissue type does not exceed 200 μm.

18 Claims, 17 Drawing Sheets

U.S. PATENT DOCUMENTS

| 2005/0249731 A1 | 11/2005 | Aslan et al. |
| 2008/0112936 A1 | 5/2008 | Aslan et al. |
| 2009/0035349 A1 | 2/2009 | Gazit et al. |

FOREIGN PATENT DOCUMENTS

| WO | WO 93/00050 | 1/1993 |
| WO | WO 00/48576 | 8/2000 |
| WO | WO 01/10421 | 2/2001 |
| WO | WO 01/11011 | 2/2001 |
| WO | WO 02/087411 | 11/2002 |
| WO | WO 2004/007697 | 1/2004 |

OTHER PUBLICATIONS

Official Action Dated Oct. 17, 2007 From the US Patent and Trademark Office Re.: U.S. Appl. No. 10/520,271.

Official Action Dated Jun. 27, 2008 From the US Patent and Trademark Office Re.: U.S. Appl. No. 10/476,064.

Official Action Dated Nov. 28, 2007 From the US Patent and Trademark Office Re.: U.S. Appl. No. 10/476,064.

Communication Pursuant to Article 94(3) EPC Dated Feb. 25, 2008 From the European Patent Office Re.: Application No. 03764110.7.

Official Action Dated Jun. 10, 2009 From the US Patent and Trademark Office Re.: U.S. Appl. No. 12/007,954.

Aslan et al. "Osteogenic Differentiation of Noncultured Immunoisolated Bone Marrow-Derived CD105+ Cells", Stem Cells, 24(7): 1728-1737, 2006.

Caplan et al. "Mesenchymal Stem Cells: Building Block for Molecular Medicine in the 21st Century", Trends in Molecular Medicine, 7(6): 259-264, 2001.

Clarke et al. "Mesenchymal Cell Precursors From Human Bone Marrow Have a Phenotype That Is Distinct From Cultured Mesenchymal Cells and Are Exclusively Present in a Small Subset of CD451° SH2+ Cells", Blood, 98(11 Part 1): 85a, 2001. Abstract # 355.

Devine et al. "Mesenchymal Stem Cells Are Capable of Homing to the Bone Marrow of Non-Human Primates Following Systemic Infusion", Experimental Hematology, 29(2): 244-255, 2001.

Fridenshtein "Stromal Bone Marrow Cells and the Hematopoietic Microenvironment", Arkh Patol, 44(10): 3-11, 1982. Abstract.

Gronthos et al. "The Growth Factor Requirements of STRO-1-Human Bone Marrow Stromal Precursors Serum-Deprived Conditions in Vitro", Blood, 85(4): 992-940, 1995.

Haynesworth et al. "Characterization of Cells With Osteogenic Potential From Human Marrow", Bone, 13: 81-88, 1992.

Horowitz et al. "Transplantability and Therapeutic Effects of Bone Marrow-Derived Mesenchymal Cells in Childern With Osteogenesis Imperfecta", Nature Medicine, 5(3): 309-313, 1999.

Kadiyala et al. "Culture Expanded Canine Mesenchymal Stem Cells Possess Osteochondrogenic Potential in Vivo and in Vitro", Cell Transplantation, 6(2): 125-134, 1997.

Keunmyoung et al. "Human Mesenchymal Stem Cells MaintainTransgene Expression During Expansionand Differentiation", Molecular Therapy, 3(6): 857-866, 2001.

Krebsbach et al. "Repair of Craniotomy Defects Using Bone Marrow Stromal Cells", Transplantation, 66(10): 1272-1278, 1998.

Liechty et al. "Human Mesenchymal Stem Cells Engraft and Demonstrate Sitespecific Differentiation After in Utero Transplantation in Sheep", Nature Medicine, 6(11): 1282-1286, 2000.

Mackay et al. "Chondrogenic Differentiation of Cultured Human Mesenchymal Stem Cells From Marrow", Tissue Engineering, 4(4): 415-428, 1998.

Majumdar et al. "Cutting Edge Communication—Human Marrow-Derived Mesenchymal Stem Cells (MSCs) Express Hematopoietic Cytokines and Support Long-Term Hematopoiesis When Differentiated Toward Stromal and Osteogenic Lineages", Journal of Hematotherapy & Stem Cell Research, 9: 841-848, 200.

Majumdar et al. Isolation, Characterization, and Chondrogenic Potential of Human Bone Marrow-Derived Multipotential Stromal Cells, Journal of Cellular Physiology, 185: 98-106, 2000.

Pelled et al. "Mesenchymal Stem Cells for Bone Gene Therapy and Tissue Engineering", Current Pharmaceutical Design, 8: 1917-1928, 2002.

Pittenger et al. "Human Mesenchymal Stem Cells Can Be Directed Into Chondrocytes, Adipocytes and Osteocytes", Molecular Biology of the Cell, 305a: 1772, 1996. Abstract.

Pittenger etal. "Multilineage Potential of Adult Human Mesenchymal Stem Cells", Science, 284(5411): 143-147, 1999.

Quirici et al. "Isolation of Bone Marrow Mesenchymal Stem Cells by Anti-Nerve Growth Factor Receptor Antibodies", Experimental Hematology, 30(7): 783-791, 2000.

Toma et al. "Human Mesenchymal Stem Cells Differentiate to a Cardiomyocyte Phenotype in the Adult Murine Heart", Circulation, 105: 93-98, 2002.

Turgeman et al. "Cell-Mediated Gene Therapy for Bone Formation and Regeneration", Current Opinion in Molecular Therapeutics, 4(4): 390-394, 2002.

Turgeman et al. "Engineered Human Mesenchymal Stem Cells: a Novel Platform for Skeletal Cell Mediated Gene Therapy", The Journal of Gene Medicine, 3: 240-251, 2001.

Yoo et al. "The Cohondrogenic Potential of Human Bone-Marrow-Derived Mesenchymal Progenitor Cells", Journal of Bone and Joint Surgery, 80(12): 1745-1757, 1998.

Young et al. "Use of Mesenchymal Stem Cells in a Collagen Matrix for Achilles Tendon Repair", Journal of the Orthopaedic Research, 16: 406-413, 1998.

Cordewener et al. "The Future of Biodegradable Osteosyntheses", Tissue Engineering, 6(4): 413-424, 2000.

Heath "Cells for Tissue Engineering", TIBTECH, 18: 17-19, 2000.

Kaihara et al. "Silicon Micromachining to Tissue Engineer Branched Vascular Channels for Liver Fabrication", Tissue Engineering, 6(2): 105-117, 2000.

Langer et al. "Tissue Engineering: The Challenges Ahead. The Obstacles to Building New Organs From Cells and Synthetic Polymers Are Daunting But Surmountable", Scientific American, p. 86-89, 1999.

Schmidt et al. "Acellular Vascular Tissues: Natural Biomaterials for Tissue Repair and Tissue Engineering", Biomaterials, 21: 2215-2231, 2000.

Stock et al. "Tissue Engineering: Current State and Prospects", Annu. Rev. Med., 52: 443-451, 2001. Abstract.

Vathsala "Meeting the Challenges of Transplantation", Transplantation Proceedings, 32: 1456-1459, 2000.

Caplan "Tissue Engineering Designs for the Future: New Logics, Old Molecules", Tissue Engineering, 6(1): 1-8, 2000. Also in: Immunity, 14(4): 425-436, 2001.

Clarke et al. "Mesenchymal Cell Precursors From Human Bone Marrow Have a Phenotype That Is Distinct From Cultured Mesenchymal Cells and Are Exclusively Present in a Small Subset of CD451? SH2+ Cells", Blood, 98(11 Part 1): 85a, 2001. Abstract # 355.

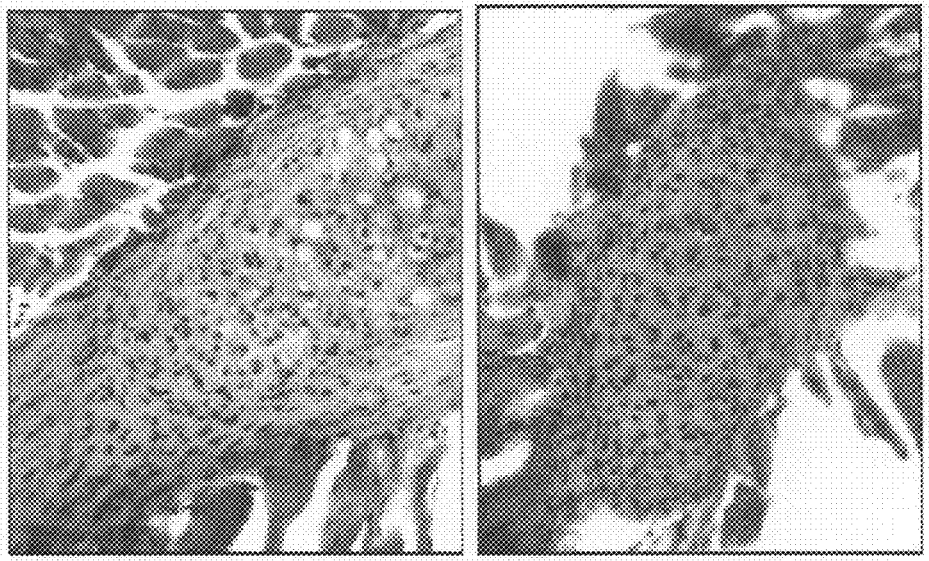
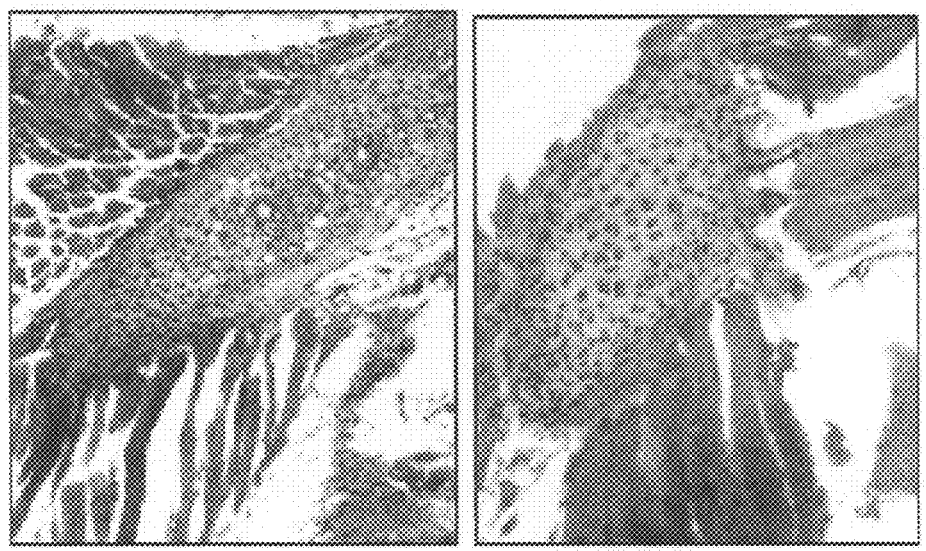
Fig. 6

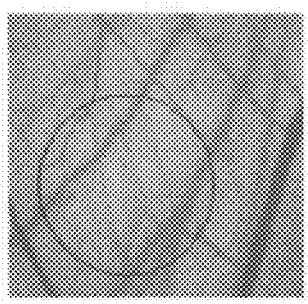
Fig. 10h
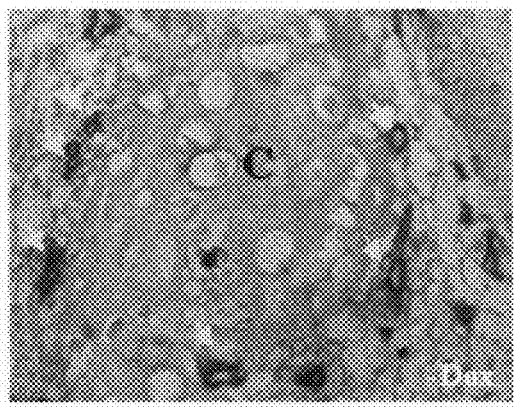
Fig. 10f
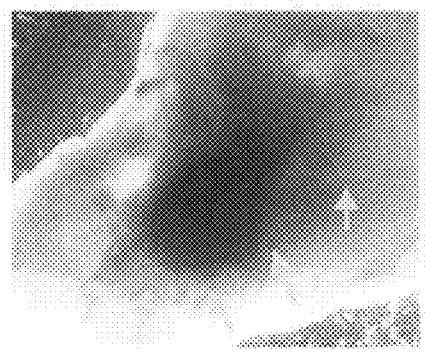
Fig. 11a
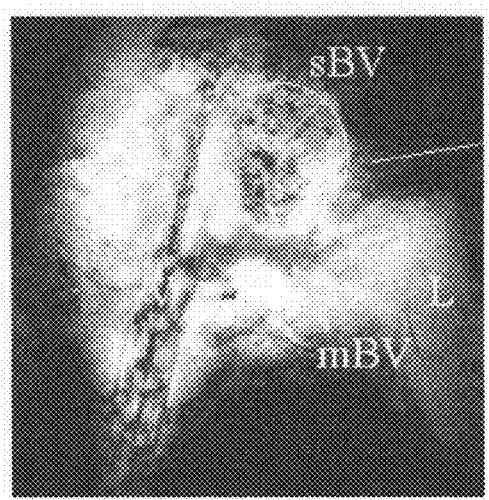
Fig. 11b
Unseeded polymeric filament
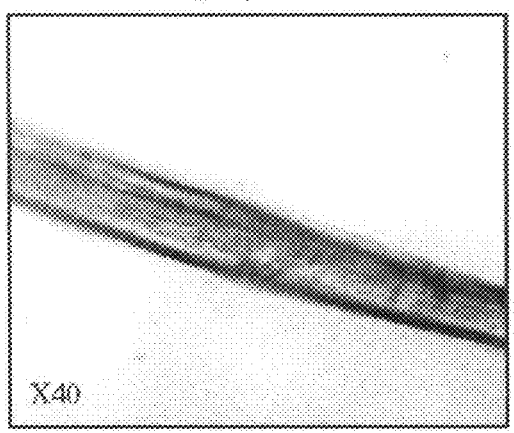
Polymeric filament seeded with b-END-2 cells
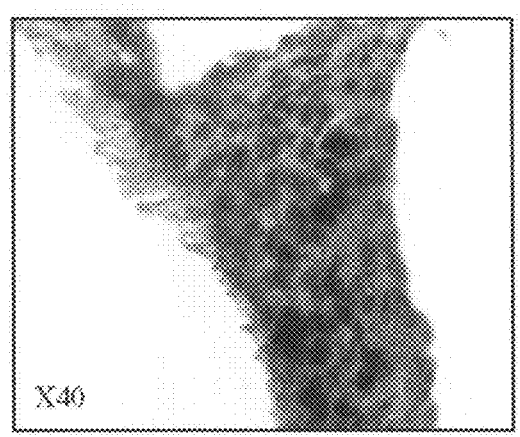
Fig. 12

— 343 bp

COMPOSITE SCAFFOLDS AND METHODS USING SAME FOR GENERATING COMPLEX TISSUE GRAFTS

RELATED APPLICATIONS

This application is a Continuation of U.S. patent application Ser. No. 10/476,064, filed on May 25, 2004, now abandoned and which is a National Phase of PCT Patent Application No. PCT/IL02/00336 having International Filing Date of Apr. 30, 2002, which claims the benefit of U.S. Provisional Patent Application No. 60/287,003 filed on Apr. 30, 2001. The contents of the above Applications are all incorporated herein by reference.

FIELD AND BACKGROUND OF THE INVENTION

The present invention relates to composite scaffolds capable of supporting growth of complex tissue and to methods of manufacturing and using same.

Traditional medical treatments for functional deficiencies in organs have focused on using pharmaceutical compositions for replacing such functional deficiencies. However, in some cases, pharmaceutical replacement therapy cannot be instated since organ function is oftentimes complex and/or not completely understood.

In such cases, the only viable alternative is surgical replacement of the non-functional organ, however, in most cases, organ transplantation requires continuous use of immunosuppressive agents to prevent immunological rejection of the organ, depriving the patient of the full protective function of the immune system.

Moreover, the need for donor organs far exceeds the supply. Organ shortage has resulted in new surgical techniques, such as splitting adult organs for transplant. Despite fairly good results, such techniques still suffer from a lack of donor tissue.

The lack of viable donor tissue has led to the emergence of methods directed at generating engineered tissue for use in replacement procedures. Such methods typically employ a physical matrix for generating a three dimensional ex-vivo cell culture (see, for example, U.S. Pat. Nos. 4,060,081; 4,485,097; 4,458,678; 4,520,821; 5,041,138; 5,786,217; 5,855,610; and 6,143,293).

The basic concept of tissue engineering employs a scaffold (matrix) which provides a support upon which seeded cells can organize and develop into desired tissue prior to implantation. The scaffold provides an initial biomechanical profile for the replacement tissue until the cells can produce an adequate extracellular matrix. During the formation, deposition and organization of the newly generated matrix, the scaffold is either degraded or metabolized, eventually leaving engrafted tissue in its place.

Typically scaffolds are manufactured from biocompatible materials such that implantation thereof does not result in an adverse immune response or induced toxicity. In addition, scaffolds are typically manufactured with predetermined porosity so as to facilitate loading thereof of drugs or nutrients useful in promoting the growth of implanted cells.

Scaffold Manufacturing Approaches:

Fabrication of an appropriate scaffold, is determined by the type of tissue to be generated. Various scaffold manufacturing procedures rely on fabrication and casting of polymeric foams. Most of the polymeric foams used for tissue engineering applications are made from polylactides (PLA), polyglycolides (PGA), or a combination of the two (PLGA).

Development of polymers, especially biodegradable polymers that produce non-toxic degradation products, as well as processing techniques to prepare porous three dimensional scaffolds with highly interconnected pore networks has become an important area of research.

Fiber bonding: Fiber bonding is a technique commonly for preparing structural interconnecting fiber networks for organ implants. Utilizing this process non-woven fibers are bonded together by immersing a non-bonded fiber structure of polymer A, such as PGA with a solution of polymer B (e.g., poly-L-lactic acid) (PLLA) using a solvent which does not dissolve polymer A. The solvent is then allowed to evaporate. The composite consisting of polymer A fibers embedded in a matrix of polymer B is heated above the melting temperature of polymer A to bond the fibers at their cross-points, and then polymer B is selectively dissolved (Mikos, et al. 1993 J. Biomed. Matl. Res. 27:183-189). The resultant bonded fiber structure of Polymer A has substantial rigidity, but the number of pores and their distribution is limited by that of the fiber mesh used in the fabrication.

Solvent-casting and particulate-leaching: In this technique, sieved salt particles, such as sodium chloride crystals, are spread in a PLLA/chloroform solution which is then used to cast a membrane. After evaporating the solvent, the PLLA/salt composite membranes are heated above the PLLA melting temperature and then quenched or annealed by cooling at controlled rates to yield amorphous or semi-crystalline forms with regulated crystallinity. The salt particles are eventually leached out by selective dissolution to produce a porous polymer matrix (Mikos, et al. 1992 Biodegradable Materials Research Society Symposium Proceedings, 252:352-358). However, the maximum level of porosity in this process is limited due to the difficulty of suspending salt particulates in the polymer solution. Furthermore, the crystalline structure of the sodium chloride salts gives rise to sharp edges which line the pores of the resulting foam, substantially reducing cell growth within the pores. Some of these problems can be overcome by making thin films of the foam and laminating them. Nevertheless, complex shaped implants cannot be easily compacted and the process is rather time-consuming.

Melt molding: Melt molding uses a Teflon™ mold, a mixture of fine PLGA powder and gelatin microspheres is heated above the glass-transition temperature of the polymer. The PLGA-gelatin composite is then removed from the mold and gelatin microspheres are leached out by selective dissolution in distilled de-ionized water.

Many of the above-described scaffold fabrication techniques generate scaffolds with inherent limitations.

Since such techniques require the use of severe heat or chemical treatment steps, cell seeding cannot be initiated during scaffold fabrication. In addition, chemical treated scaffolds can often invoke an inflammatory response following implantation.

Vascularization of an Engineered Tissue:

The need for a vascular network in engineered tissue has been demonstrated in studies of hepatocytes transplantation (Mooney et al. 1997). which demonstrated that survival of hepatocytes transplanted in vivo can be as low as 10% several days following transplantation, for a lack of ample vascularization. Similar findings were observed with transplants of smooth muscle cells (Cohn et al. 1997, Colton 1995).

To date most methods aimed at increasing implant permeability to nutrients, growth factors and oxygen rely on passive diffusion or alternatively external lining of the implant with artificial blood vessels.

Although numerous scaffold designs suitable for generating engineered tissues are known in the art, tissues engineered using such scaffolds typically lack the full functional capabilities of natural tissues. This is due to the fact that such scaffolds are either incapable of generating complex tissues having a fully functional architecture (e.g., vascularized), or are incapable of supporting growth of complex tissues altogether.

There is thus a widely recognized need for, and it would be highly advantageous to have, scaffolds which can be used to generate complex tissue grafts, such as, for example, vascularized tissue grafts, either ex-vivo or in-vivo while being devoid of the limitations inherent to prior art scaffolds.

SUMMARY OF THE INVENTION

According to one aspect of the present invention there is provided a composite scaffold for engineering a heterogeneous tissue, the composite scaffold comprising: (a) a first scaffold being capable of supporting formation of a first tissue type thereupon; and (b) a second scaffold being capable of supporting formation of a second tissue type thereupon; wherein the first scaffold and the second scaffold are arranged with respect to each other such that when the first scaffold supports the first tissue type and the second scaffold supports the second tissue type, a distance between any cell of the second tissue type and the first tissue type does not exceed 200 µm.

According to further features in preferred embodiments of the invention described below, there is provided an engineered tissue graft generated using the composite scaffold described above.

According to another aspect of the present invention there is provided a method of inducing the formation of a heterogeneous tissue, the method comprising: (a) providing a first scaffold being capable of supporting formation of a first tissue type thereupon; (b) providing a second scaffold being capable of supporting formation of a second tissue type thereupon; (c) embedding the first scaffold in the second scaffold thereby forming a composite scaffold; and (d) implanting the composite scaffold in an individual.

According to still further features in the described preferred embodiments the step of embedding is effected such that when the first scaffold supports the first tissue type and the second scaffold supports the second tissue type, a distance between any cell of the second tissue type and the first tissue type does not exceed 200 µm.

According to still further features in the described preferred embodiments the first scaffold is a filamentous scaffold having filaments of a diameter selected from the range of 4-500 µm.

According to still further features in the described preferred embodiments the second scaffold is a porous continuous scaffold.

According to, still further features in the described preferred embodiments the filamentous scaffold is selected so as to enable the first tissue type to form substantially tubular structures thereupon.

According to still further features in the described preferred embodiments the first tissue type is vascular tissue.

According to still further features in the described preferred embodiments the second tissue type is structural tissue selected from the group consisting of bone tissue, cartilage tissue, adipose tissue, connective tissue and muscle tissue.

According to still further features in the described preferred embodiments the first scaffold and/or the second scaffold further include a bioactive agent associated therewith.

According to still further features in the described preferred embodiments the bioactive agent is selected from the group consisting of a cell proliferation factor, a cell differentiation factor, a cell attracting factor and a pharmacologically active factor.

According to still further features in the described preferred embodiments the step of growing the first tissue type on the first scaffold and/or growing the second tissue type on the second scaffold prior to step (c).

According to still further features in the described preferred embodiments the method further comprising growing the second tissue type on the second scaffold prior to step (c) or step (d).

According to still further features in the described preferred embodiments the first scaffold is selected so as to enable colonization and/or proliferation of at least one cell type composing the first tissue type.

According to still further features in the described preferred embodiments the second scaffold is selected so as to enable colonization and/or proliferation of at least one cell type composing the second tissue type.

According to still further features in the described preferred embodiments the first scaffold and/or second scaffold are degradable upon exposure to predetermined environmental conditions.

According to still further features in the described preferred embodiments the predetermined environmental conditions are selected from the group consisting of presence of hydrolytic enzymes, presence of proteasomal enzymes, pH lower than 5 and reducing conditions.

According to yet another aspect of the present invention there is provided a composition of matter comprising: (a) a linker molecule attached to a first polymer backbone; (b) a stereoisomer of the linker molecule attached to a second polymer backbone; wherein when exposed to polymerizing conditions the first and the second polymer backbones cross-link with at least one molecule of the first and/or the second polymer backbones via at least one of the linker molecule and the stereoisomer of the linker molecule to thereby form a scaffold structure.

According to still further features in the described preferred embodiments the first polymer backbone is identical to the second polymer backbone.

According to yet another aspect of the present invention there is provided a composition of matter comprising a polymer backbone attached to: (a) a linker molecule; and (b) a stereoisomer of the linker molecule; wherein when exposed to polymerizing conditions the polymer backbone cross links with at least an additional polymer backbone via at least one of the linker molecule and the stereoisomer of the linker molecule, to thereby form a scaffold structure.

According to still further features in the described preferred embodiments the linker molecule is a co-polymer of lactic acid.

According to still further features in the described preferred embodiments the scaffold structure is three-dimensional.

According to yet another aspect of the present invention there is provided a scaffold comprising a plurality of molecules of a polymeric backbone cross-linked therebetween via L and D stereoisomers of a linker molecule.

According to still further features in the described preferred embodiments the polymer backbone is a hydrophilic polymer.

According to still further features in the described preferred embodiments the hydrophilic polymer is selected from the group consisting of a natural polysaccharide, a protein, an ethylene glycol based polymer and a propylene glycol based polymer.

According to still further features in the described preferred embodiments the plurality of molecules of the polymeric backbone are hydrophilic polymers.

According to still further features in the described preferred embodiments the hydrophilic polymers are selected from the group consisting of natural polysaccharides, proteins, ethylene glycol based polymers and a propylene glycol based polymers.

According to still another aspect of the present invention there is provided a scaffold capable of releasing a bioactive agent, the scaffold comprising a polymeric backbone and the bioactive agent, wherein the polymeric backbone is selected such that exposure thereof to predetermined environmental conditions leads to release of the bioactive agent from the scaffold.

According to still further features in the described preferred embodiments the bioactive agent is selected from the group consisting of a cell proliferating factor, a cell differentiating factor, a cell attracting factor and a pharmacologically active factor.

According to still further features in the described preferred embodiments the polymeric backbone is selected from the group consisting of cellulose, hydroxy alkyl acid polyester, polyphosphazene, polycarbonate, lactide acid and glycolide acid.

According to still further features in the described preferred embodiments the bioactive agent is incorporated within the polymeric backbone, and whereas the bioactive agent is released following degradation and/or disintegration of the polymeric backbone in the environmental conditions.

According to still further features in the described preferred embodiments the bioactive agent is a negatively charged bioactive agent, and whereas the negatively charged bioactive agent is incorporated within pre-cationized regions of the polymeric backbone.

According to still further features in the described preferred embodiments the polymeric backbone is designed and constructed so as to enable timed release of the bioactive agent from the scaffold. According to still further features in the described preferred embodiments the predetermined environmental conditions are selected from the group consisting of presence of hydrolytic enzymes, presence of proteasomal enzymes, presence of pH lower than 5 and presence of reducing conditions, According to an additional aspect of the present invention there is provided a scaffold comprising a filamentous polymer including: (a) a hydrophilic molecule being capable of promoting degradation of the filamentous polymer when exposed to predetermined environmental conditions; (b) a plasticizing agent being capable of rendering the filamentous polymer flexible; and (c) a co-polymeric stereocomplex being capable of cross linking the filamentous polymer with at least one additional filamentous polymer to thereby form the scaffold.

According to still further features in the described preferred embodiments the filamentous polymer has a diameter selected from a range of 4-500 μm.

According to still further features in the described preferred embodiments the filamentous polymer is designed and configured for supporting formation of a tube shaped tissue structure thereupon According to still further features in the described preferred embodiments the filamentous polymer is selected from the group consisting of hydroxy alkyl acid polyester, polyphosphazene, poly carbonate and poly phosphate ester.

According to still further features in the described preferred embodiments the filamentous polymer is degradable upon exposure to predetermined environmental conditions.

According to still further features in the described preferred embodiments the predetermined environmental conditions are selected from the group consisting of presence of hydrolytic enzymes, presence of proteasomal enzymes, pH lower than 5 and reducing conditions.

According to still further features in the described preferred embodiments the tube shaped tissue is vascular tissue.

According to still further features in the described preferred embodiments the hydrophilic molecule is poly ethylene glycol and poly ethylene propylene glycol.

According to still further features in the described preferred embodiments the plasticizing agent is selected from the group consisting of a tributyl citrate, a tributyl citrate acetate, a phospholipids and an oleate ester.

According to still further features in the described preferred embodiments the co-polymeric stereocomplex includes lactide acid stereoisomers.

According to still further features in the described preferred embodiments the scaffold further comprising a bioactive agent associated therewith.

According to still further features in the described preferred embodiments the bioactive agent is selected from the group consisting of a cell proliferation factor, a cell differentiation factor, a cell attracting factor and a pharmacologically active factor.

The present invention successfully addresses the shortcomings of the presently known configurations by providing novel scaffold configurations which can be used, ex-vivo and/or in-vivo, to generate complex tissue, such as, for example, vascularized tissues and organs like liver, pancreas, kidney and the like.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3a is a schematic depicting liposome complexation of a plasmid encoding β-galactosidase and transfection of a target cell. FIGS. 3b and 3c are low- and high-power magnification photomicrographs, respectively, demonstrating β-galactosidase production by a murine mesenchymal stem cell line transfected in vitro with a liposome-complexed plasmid encoding a β-galactosidase marker gene.

FIG. 4a is a schematic depicting dextran polycation complexation of a plasmid encoding β-galactosidase and transfection of a target cell. FIGS. 4b and 4c are low- and high-power magnification photomicrographs, respectively, demonstrating β-galactosidase production by a murine mesenchymal stem cell line transfected in vitro with a dextran polycation-complexed plasmid encoding a β-galactosidase marker gene.

FIG. 6 is a series of photomicrographs depicting chondrogenesis and osteogenesis induced by in vivo implantation of arabinogalactan-chitosan cellular scaffolds loaded with naked and liposome-complexed plasmid encoding human BMP-2.

FIGS. 8a and 8f are macrophotographs depicting growth and differentiation of tissue in the absence (−Dox) and presence (+Dox) of doxycycline, respectively. FIG. 8o depicts the presence and absence of BMP-2 mRNA transcription in the absence and presence of doxycycline, respectively, in engrafted cells (C9) on Day 10, as determined by RT-PCR analysis.

FIG. 9 depicts the orthotopic regeneration of bone tissue by implantation of collagen matrices seeded with MSCs genetically modified to express BMP-2 (C9).

FIG. 10 depicts in vivo vascularization induced in collagen matrix implants seeded with MSCs genetically modified to express BMP-2 under the regulatory control of a tetracycline/doxycycline-inhibited promoter, angiogenesis induced by 10 μg BMP-2 in chick CAM assays and angiogenesis induced in vivo in bone tissue formed by culturing cellular scaffolds seeded with MSCs genetically modified to express BMP-2. FIG. 10f is a photomicrograph depicting blood vessel formation in collagen matrix implants seeded with MSCs genetically modified to express BMP-2, as determined by immunohistochemical staining of the endothelial marker PECAM. FIGS. 10g and 10h are photomicrographs depicting angiogenesis induced by 10 μg of human BMP-2 protein and vehicle as control in chick CAM assays, respectively.

FIGS. 11a-b depicts angiogenesis induced in vivo in bone tissue formed by culturing cellular scaffolds seeded with MSCs genetically modified to express BMP-2, as determined by microscopic and MRI analyses. FIG. 11a is a low photomicrograph of the implant (arrows indicate blood vessels). FIG. 11b represents MRI data of the area including the implant (sBV: small blood vessels, mBv: large blood vessel, L: hind limb, V: vertebral column).

FIG. 12 is a photomicrograph depicting formation of vascular tissue upon filamentous cellular scaffolds cultured in vitro with endothelial cells.

FIG. 13a depicts low and high-power photomicrographs of seeded implants two weeks after incubation in rotating bioreactor (endothelial cells depicted by arrows). FIG. 13b depicts low power photomicrographs of a seeded/non-implanted scaffold ("Ex Vivo") and seeded and non-seeded implants two weeks after implantation. P: polymer.

FIG. 14a—empty scaffold; FIG. 14b—C9 cells on scaffold; FIG. 14c—collagen II detection via RT-PCR; FIG. 14d—H&E staining; FIG. 14e—anti Osteocalcin staining; FIG. 14f—anti βgalactosidase staining; FIG. 14g—anti collagen X staining.

FIG. 2a clearly illustrates cells attached to the polymeric structure. The cells were stained with a fluorescent stain (propidium iodide) and were seen in different optic sections within the scaffold. The image presented in FIG. 15b is a computerized reconstruction of all optic sections (the different colors represent different distance from the surface of the scaffold).

DESCRIPTION OF THE PREFERRED EMBODIMENTS

Figure 1:
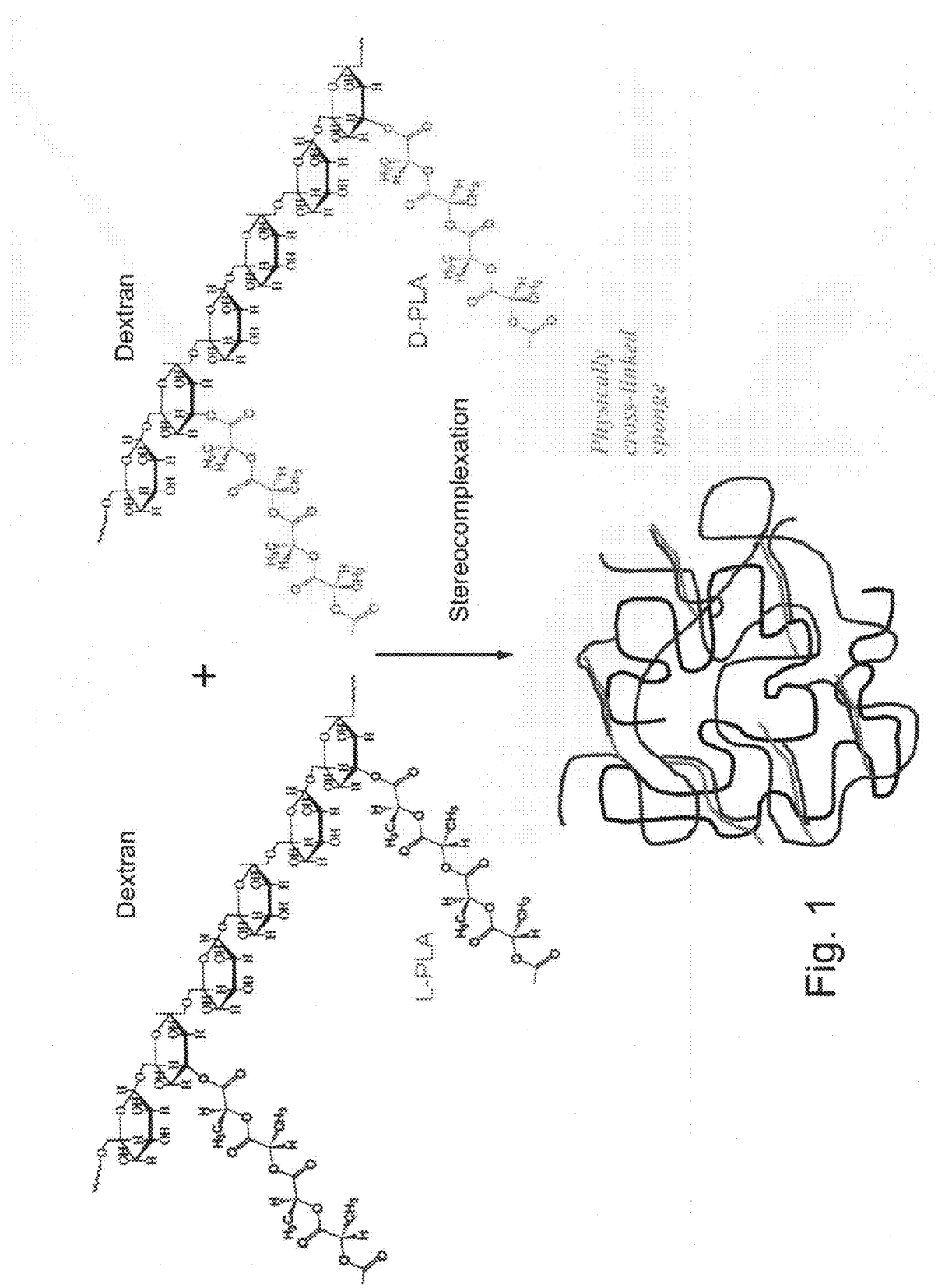
FIG. 1 depicts formation of a cross-linked polymeric cellular scaffold generated by stereocomplexation of dextran with poly-D and poly-L lactic acids.

The present invention is of novel polymeric compositions and methods of using same for engineering complex tissue. Specifically, the present invention can be used to generate complex tissue grafts composed of at least two tissue types co-arranged in a functional architecture.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings described in the Examples section. The invention is capable of other embodiments or of being practiced or carried out in various ways. Also, it is to be understood that the phraseology and terminology employed herein is for the purpose of description and should not be regarded as limiting.

The increasing disparity between demand and availability of human donor organs has prompted an intensive search for alternative approaches to organ replacement therapy.

The bioartificial implant is one proposed solution. However, presently fabricated bioartificial implants has proven to be unsatisfactory for a variety of reasons, including, poor biocompatibility, engraftment failure or tissue dysfunction.

One of the major problems of bioartificial implants is the need for a well branched vascular network, which can providing the engineered tissue with continuous supply of oxygen and nutrients at the transplantation site. To date all attempts to address this issue have resulted in poor vascularization of engrafted tissues.

The present invention provides a novel approach for engineering complex tissues, such as vascularized structural tissues, thus substantially enhancing the acceptance rate of engrafted engineered tissue.

As illustrated hereinunder and in the Examples section which follows, the complex tissues of the present invention are generated using novel composite scaffolds and in-vivo and/or ex-vivo tissue engineering approaches.

Thus, according to one aspect of the present invention there is provided a composite scaffold for engineering a heterogeneous tissue.

As used herein, the term "scaffold" refers to an engineered platform which serves as a physical substrate for cell colonization and/or proliferation.

A "composite scaffold" refers to a substrate which is engineered in order to support colonization and/or proliferation of two or more tissue types which together comprise a "heterogeneous tissue".

Thus, the composite scaffold of the present invention includes a first scaffold for supporting formation of a first tissue type thereupon and a second scaffold for supporting formation of a second tissue type thereupon.

According to one preferred embodiment of the present invention, the first scaffold and the second scaffold are arranged with respect to each other such that when the first scaffold supports the first tissue type and the second scaffold supports the second tissue type, a distance between any cell of the second tissue type and the first tissue type does not exceed 200 µm. Such an arrangement ensures that a functional architecture is maintained within the heterogeneous tissue formed upon the scaffold.

For example, in cases where the heterogeneous tissue is vascularized structural tissue, such scaffold arrangement ensures cell viability by providing diffusion of nutrients and gases such as oxygen to every cell in the tissue graft formed, as well as diffusion of cellular waste out of the graft so as to minimize cellular toxicity and concomitant death due to localization of the waste within graft tissues.

The design of the composite scaffold of the present invention is dictated by cellular organization of natural tissue which is to mimicked by the scaffold-engineered tissue. For example, it has been previously shown that organ tissue is arranged into functional units composed of cells, each no more than 225 µm away from a source of nutrients (see, PCT/US98/00594). Such organization ensures efficient gas and nutrient exchange and thus cell viability and functionality. Thus, in cases where the composite scaffold of the present invention is used for engineering an organ tissue graft, such a composite scaffold will have at least two scaffold components arranged such that tissue formed thereupon would mimic the cellular arrangement of an organ functional unit.

Thus, the composite scaffold of the present invention is designed such that tissue engineered thereupon would exhibit a spatial distribution of cellular elements which closely approximates that found in the counterpart tissue in vivo. This would enable rapid engraftment of the engineered tissue while ensuring a high rate of survival of graft tissue during the engraftment process.

The composite scaffold of the present invention is generated from at least two different scaffold structures. Each scaffold structure is composed of scaffold material and microstructure suitable for organizing and stimulating the growth of a specific cell type.

For example, in the case of a vascularized structural tissue, the composite scaffold of the present invention includes a filamentous scaffold for supporting colonization/proliferation of vascular tissue forming cells and a continuous scaffold for supporting colonization/proliferation of cell types which form the structural tissue.

The composite scaffold of the present invention is designed so as to allow complete co-integration of the two different scaffolds, enabling the formation of a heterogeneous tissue which maintains a functional architecture. In the case of vascularized structural tissue, the continuous scaffold is preferably arranged around the filamentous scaffold such that the structural tissue encapsulates the vascular tissue.

The various scaffold components of the composite scaffold of the present invention are preferably generated from biocompatible material especially in cases where the scaffold is utilized for in-vivo generation of heterogeneous tissue as is described in detail hereinbelow.

The term "biocompatible" refers to a substance which does not induce an immune response or fibrosis. Examples of biocompatible materials include, but are not limited to, polysaccharides, alginates, polyalcohols, organic acids, agarose, agarose/poly(styrene sulfonic acid), hydroxyethyl methacrylate-methyl methacrylate copolymer, polyvinyl alcohol and protamine-heparin.

The various scaffold components of the composite scaffold of the present invention are also preferably generated from biodegradable material especially in cases where it is important to get rid of scaffold material following tissue formation.

The term "biodegradable" refers to material which is chemically degraded by the action of hydrolytic enzymes, proteolytic enzymes, extreme pH conditions, and the like. Examples of biodegradable materials include polymer compositions such as polyhydroxy acids, modified polysaccharides and combinations thereof.

As mentioned hereinabove, a composite scaffold for supporting vascularized structural tissue preferably includes two scaffold structures, a filamentous scaffold for the formation of vascular tissue and a continuous scaffold for the formation of the structural tissue. Following is a detailed description of these two scaffold structures.

Filamentous Scaffold:

The generation of a filamentous scaffold according to the present invention takes into account the following considerations:

(i) Filaments must remain intact during cell adherence and growth thereupon, but at the same time must rapidly erode within 14-30 days thereafter to obtain a functional blood vessel with a continuous lumen which supports blood flow.

(ii) Efficient adherence of cells to the filamentous scaffold followed by cell proliferation around the filamentous scaffold to form a continuous and uniform cell layer. Preferably, the filamentous scaffold of the present invention is a solid scaffold capable of supporting cell growth thereupon. Such a scaffold can mimic a blood vessel lumen and form a blood vessel having even small capillary diameter of 4-50 microns.

(iii) The filamentous scaffold must be strong and flexible enough to allow formation of flexible thin filaments having a diameter ranging between 4-500 microns.

Various types of biodegradable polymers meet these criteria, including, for example, thin cellulose fibers. Cellulose fibbers can be modified by oxidation with, for example, periodate in aqueous medium, rendering the fibers more susceptible to hydrolytic degradation (biodegradation). The degree of oxidation determines the strength of the fiber and its degradation profile. These oxidized fibers can be further modified by impregnation with a biodegradable polymer such as poly (lactide-glycolide) so as to be more susceptible to biological degradation. Optionally, fiber aldehyde groups can be reacted with amino containing hydrophilic or hydrophobic safe molecules including amino acids.

Alternatively, polymers and copolymers based on hydroxy alkyl acid polyesters, polyphosphazene, poly(carbonates) and poly(phosphate esters), can also be used. Polymers based on lactide and glycolide acids are better suited for use with the filamentous scaffold of the present invention since it has been previously shown that such materials are capable of supporting cell growth and can be safely transplanted in humans (Shand and Heggie 2000).

These polymers can also be modified to meet the requirements described above. For example, block and random copolymers of lactide acid and glycolic acid having a molecular weight greater than 10,000, can be spun into thin filaments. To prevent accelerated erosion when exposed to an environment enriched with degrading enzymes, copolymers including 30 to 70% lactic acid may be used to delay degradation to a few weeks post transplantation.

Increased flexibility of the filaments can be obtained by adding plasticizing agents such as, for example, tributyl citrate, tributyl citrate acetate, phospholipids, oleate esters and the like to the polymer blend or by incorporating agents, such as, for example, ricinoleic acid into the polymer chain.

The mechanical properties of the filamentous scaffold must be maximized when supporting formation of a blood vessel such as an artery, which has to exhibit resistance to high blood pressure. This can be achieved by various cross-linking methods, interlinking the filamentous polymers, described herein above.

Preferably, cross linking is achieved via stereocomplexation which utilizes stereoisomers, such as the stereoisomers of copolymer of lactic acid, as linker molecules for stereo-cross-linking the polymer backbone (see Example 1 of the Examples section for further detail).

Continuous Scaffold:

The continuous scaffold of the present invention is designed so as to support tissue formation in and around the filamentous scaffold. The continuous scaffold can be composed of any of the polymers described hereinabove and/or any other polymers suitable for supporting structural tissue colonization/proliferation.

For example, polysaccharide such as dextran, arabinogalactan, chitosan, alginates, pullulan, hyaluronic acid, and the like, and proteins such as gelatine, collagen, fibrin, fibrinogen, albumin, and the like, can be used to form a continuous (cross linked) scaffold with a predetermined pore size. Alternatively, synthetic polymers such as, lactide and glycolide foams can also be used.

Preferably, the continuous scaffold component is generated under mild conditions. This enables to form the continuous scaffold component over a filamentous scaffold component which is already seeded with cells. Compositions based on viscous hyaluronic acid solutions, alginates cross-linked by calcium salts and proteins cross-linked by denaturation or non-harmful molecules can be used to form the continuous scaffold component over an already seeded filamentous scaffold component.

Alternatively, stereocomplexed hydrophilic polymers including, natural polysaccharides, proteins, and polymers based on ethylene and propylene glycol and mixtures thereof can also be used.

The composite scaffold or any of its components may also include a biologically active (bioactive) agent.

Various forms of bioactive agents can be incorporated into, or attached to, scaffold material. Incorporation or attachment can be configured for slow or timed release of one or more bioactive agents under suitable conditions.

Bioactive agents used are slightly water-soluble, preferably moderately water-soluble, and are diffusible through the polymeric composition. They can be acidic, basic, or salts. They can be neutral molecules, polar molecules, or molecular complexes capable of hydrogen bonding. They can be in the form of ethers, esters, amides and the like, which are biologically activated when injected into the human or animal body.

Bioactive agents suitable for use with the composite scaffold of the present invention include cytokines and growth factors for inducing proliferation/differentiation of various cell types, therapeutic agents used for the treatment, prevention, diagnosis, cure or mitigation of disease or illness, and diagnostic agents.

Examples of cytokines and growth factors include, VEGF, Ang1, Ang.-2, Ang3, PDGF, members of the Transforming Growth Factor b family, members of the Bone Morphogenetic Proteins family, members of the Fibroblasts Growth Factors family. Therapeutic agents include, but are not limited to, anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

The bioactive agent can be provided in the form of a chemical, a peptide or polypeptide, or a nucleic acid molecule which can form a part of a tissue expressible construct.

Incorporation of the active agent in the scaffolds can be performed during scaffold preparation.

For example, a negatively charged bioactive agent (such as a DNA molecule) can be attached to a pre-cationized scaffold material prior to, during or following scaffold formation.

The bioactive agent can be encapsulated within a delivery system (e.g., microspheres, liposomes) followed by attachment of the delivery system to the prepared scaffold.

Various mechanisms can be used to influence the release rate of the bioactive material following scaffold implantation. For example, the scaffold material can be formulated to degrade following implantation thereby promoting the release of the bioactive material from the scaffold. Release of a material having a low solubility in water, as for example a peptide or protein, typically requires the degradation of a substantial part of the polymer matrix to expose the material directly to the surrounding tissue fluids. Thus, the release of the biologically active material from the scaffold can be varied by, for example, the solubility of the bioactive material in water, the distribution of the bioactive material within the scaffold, or the size, shape, porosity, solubility and biodegradability of the scaffold material, among other factors.

The release of the bioactive material from the scaffold can also be controlled by varying the molecular weight of the scaffold material and by adding rate modifying agents, such as oxidizing agents or hydrophilic molecules.

In cases where the scaffold includes more than one bioactive agent, a specific rate and/or time of release may be configured for each bioactive agent. Such specific release control is particularly desired in cases where the bioactive agents are used for inducing tissue formation.

For example, in vascular tissue formation, timed release of VEGF and then angiopoietin 1,2 and 3 is imperative for efficient blood vessel formation and maturation.

The biologically active agents are used in amounts that are therapeutically effective. The effective amount of a biologically active agent will depend on the particular material being used, delivery system and releasing rate.

Succeeding in ex-vivo tissue engineering depends on meeting a variety of critical experimental conditions. One is to have the necessary components, including both regeneration-competent cells and a carrier scaffold (discussed hereinabove). Another requirement is an environment, which is conductive to cell growth, differentiation and eventually integration with the surrounding tissues following transplantation.

Thus, according to another aspect of the present invention there is provided a method of forming a heterogeneous tissue ex-vivo. For purposes of illustration the heterogeneous tissue is represented by vascularized structural tissue.

The first step typically involves building the vascular infrastructure. Vascular cells can be any cell type which can differentiate and give rise to cells lining blood vessels and capillaries, i.e., endothelial cells or pericytes from large blood vessels, skin tissue, foreskin tissue bone marrow and the like. The vascular cells are seeded onto the polymeric filaments of the filamentous scaffold, described hereinabove. This step can be effected using a spinner flask or an agitating tube. Seeded filamentous scaffold is incubated in a 37÷C incubator for 7-14 days. This results in the cover of the filamentous scaffold with vascular cells and forming a complex of branched tubular vascular structures termed as vascular bed system or vascular infrastructure (see Example 6 of the Examples section).

Various angiogenic factors which promote differentiation and maturation of vascular tissue [i.e., vascular endothelial growth factor (VEGF), angiopoietin 1, 2, 3] can be incorporated into the filamentous scaffold material as described hereinabove (see Example 6 of the Examples section hereinunder). A timed release of these factors mimics the biological state, hence enabling angiogenic differentiation and blood vessel formation.

Following formation of the angiogenic component, the vascular bed formed is embedded in a continuous scaffold.

Embedding can be effected, for example, by using aqueous solution of natural or semi-natural polysaccharides or proteins such as hyaluronic acid, alginates, oxidized cellulose, high molecular weight dextran, pullulan or arabinogalactan. Specific tissue cells, such as bone forming or muscle forming cells, can be mixed in to the colloidal dispersion and cast onto the vascular infrastructure to form a seeded composite scaffold. The cell containing continuous scaffold material can be solidified by adding gelling ingredients such as calcium salts, in case of acidic polysaccharides (i.e., alginates, hyaluronic acid, and the like) or oxidized aldehyde containing polysaccharides in case of primary amino containing proteins (i.e., gelatin, albumin, collagen, fibrin and the like) or chitosan. Alternatively, gelation can be obtained by stereocomplexation of a polysaccharide based continuous scaffold as described hereinabove.

Alternatively, the continuous scaffold solution can be cast over the filamentous scaffold and the cells seeded thereupon following polymerization. Example 4 of the Examples section which follows illustrates scaffold co-culturing of two cellular components ex-vivo.

The composite scaffold of the present invention can also be used for in-vivo tissue generation.

Thus, according to another aspect of the present invention there is provided a method of forming a heterogeneous tissue in-vivo.

Figure 2:
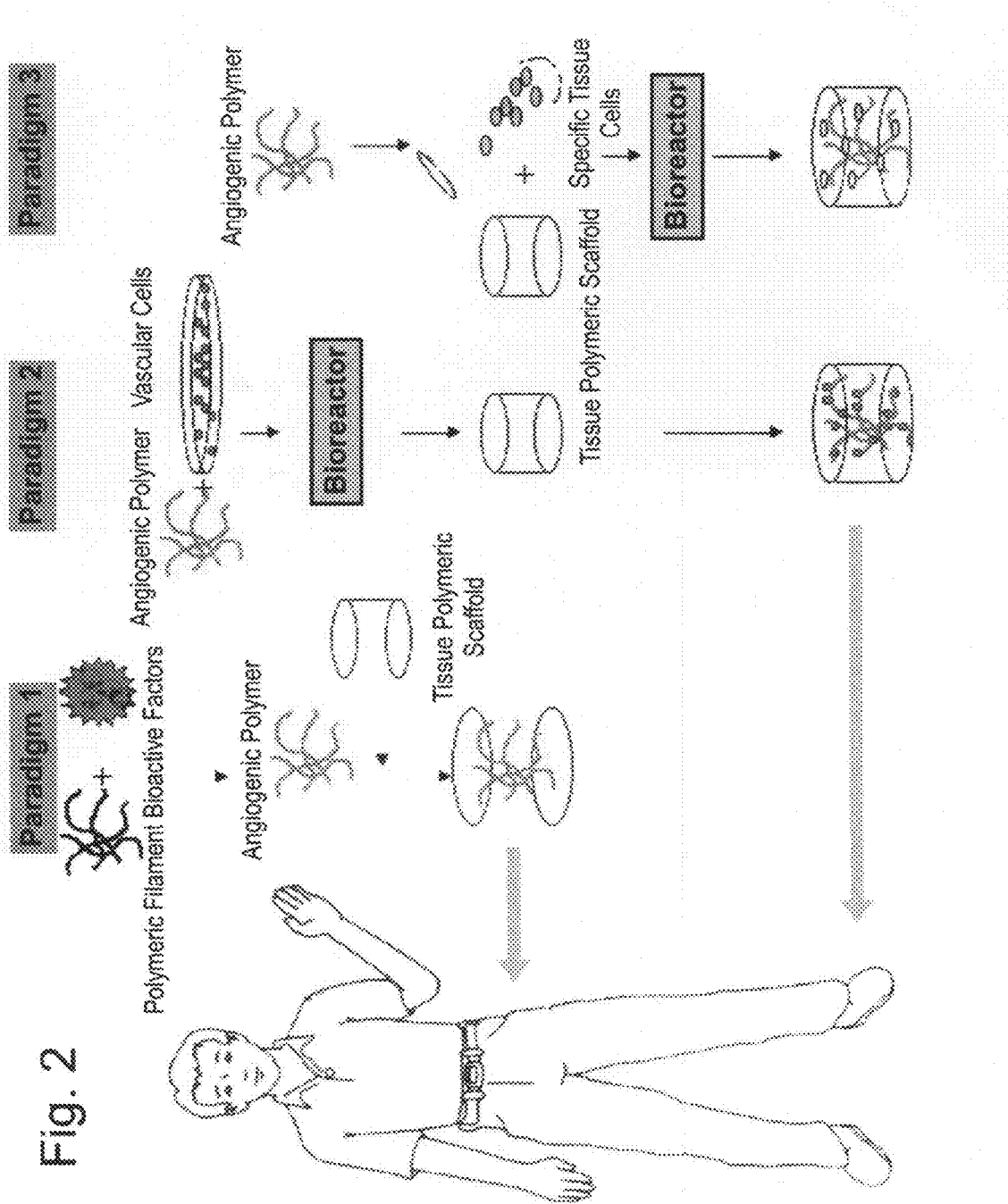
FIG. 2 depicts various combinations of in vitro and in vivo modalities for tissue replacement therapy using cellular scaffolds composed of a filamentous polymer for tubular growth of vascular tissues integrally embedded within a continuous sponge matrix polymer for three-dimensional growth of replacement tissues.

In-vivo tissue generation can be effected by implanting the composite scaffold of the present invention in an individual (see, for example, FIG. 2, Paradigm 1).

In such a case, scaffold materials preferably include bioactive agents (e.g., angiogenic factors) for promoting growth of one or more tissue types in-vivo.

The composite scaffold of the present invention can also be used for combined ex-vivo/in-vivo tissue generation.

Thus, according to another aspect of the present invention there is provided a method of forming a heterogeneous tissue combining ex vivo and in vivo tissue engineering approaches (exemplified by FIG. 2, Paradigms 2 and 3).

For example, a vascular infrastructure scaffold carrying vascular cells is embedded in the tissue continuous scaffold and the composite scaffold formed is transplanted within an individual. Transplantation of such a scaffold provides a vascular infrastructure ready to integrate with the host vascular system and as such provides optimal setting for ingrowth of tissue and regeneration.

Alternatively, and as also shown in FIG. 2 (see, Paradigm 3), structural tissue can be formed ex-vivo on a continuous scaffold surrounding a filamentous scaffold which includes angiogenic factor(s). Following implantation, the angiogenic factor(s) will promote ingrowth of capillaries and blood vessels into the engrafted structural tissue.

Thus, the present invention provides composite scaffolds and methods of using same for ex-vivo/in-vivo generation of heterogeneous tissue.

It will be appreciated that the present invention is not restricted to the scaffold/tissue formation sequence described herein, and that any scaffold/tissue formation sequence can be achieved using the composite scaffold of the present invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Oligonucleotide Synthesis" Gait, M. J., ed. (1984); "Nucleic Acid Hybridization" Hames, B. D. and Higgins S. J., eds. (1985); "Transcription and Translation" Hames, B. D. and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "*Strategies for Protein Purification and Characterization—A Laboratory Course Manual*" CSHL Press (1996); all of which are incorporated by reference as if fully set forth herein.

Example 1

Stereocomplexation of a Dextran-Based Polymeric Scaffold with Poly-D and -L Lactic Acid Improving the mechanical properties of a polymeric cellular scaffold is a major priority in the field of tissue engineering, particularly in the case of vascular tissue cell scaffolds which must exhibit high burst-strength. Such scaffolds can be mechanically strengthened by cross-linking of the polymeric backbone. In order to achieve this goal, stereocomplexation of a dextran-based polymeric scaffold was effected as follows:

Materials and Methods:

Two types of dextran-based block copolymers, one containing segments of enantiomeric D-lactic acid of at least 10 monomer units and the other composed of segments of enantiomeric L-lactic acid of at least 10 monomer units were prepared. These two copolymers were then mixed together to form specific stereocomplex interactions between the complementary D and L enantiomeric blocks along the polymer chains. Stereocomplexation of a polymeric backbone was effected by separately conjugating copolymeric chains of poly-D and -L lactic acid (PLA), having a molecular weight of 1500, to dextran 40,000 or 500,000 via the dextran hydroxyl groups.

Activation of PLA with an O-p-nitrophenyl derivative: In a glass vial, PLA (1 eq.), p-nitrophenylchloroformate (4 eq.) and triethylamine (6 eq.) were dissolved in 1 ml dichloromethane per 100 mg PLA. The mixture was stirred at room temperature overnight following which the dichloromethane was evaporated until a concentrated solution was obtained which was precipitated in isopropanol to yield PLA-O-p-nitrophenyl (>90% yield).

Conjugation of PLA-O-p-nitrophenyl to dextran: dextran (1 g), PLA-O-p-nitrophenyl (1 eq. per 10 saccharide units) and dimethylamino pyridine (DMAP, 1 eq.) were mixed in anhydrous DMSO and the mixture was hermetically stirred at room temperature for 48 hours. The mixture was then precipitated by addition of isopropanol followed by centrifugation. Dichloromethane was added to the precipitate to wash out unbound PLA residues. The degree of conjugation was evaluated by H NMR using peaks at 4.9 and 4.5 parts per million (ppm) as representative of anomeric protons and peak 5.3 ppm as a representative peak for tertiary PLA protons.

Following mixing of the solutions or dispersions of the L-PLA grafted dextran and D-PLA grafted dextran at room temperature for 24 hours cross-linking conditions, the D- and L-lactic acid oligomers along the dextran polymer chains form a three dimensional dextran matrix due to stereocomplexation of the lactide residues, as depicted in FIG. 1.

Example 2

Synthesis of a Lactide-Glycolide Polymer-Based Filamentous Cellular Scaffold for Growth of Vascular Tissue In order to optimally grow both target replacement tissues and supporting vascular tissues within a single integrated cellular scaffold, specialized subcompartments within such an integrated scaffold are required for each tissue type so as to optimize the growth of each and to establish an appropriate structural and functional relationship between the two. This can be achieved structurally via the use of a filamentous scaffold for growth of vascular tissues embedded within a continuous sponge matrix for the growth of the target replacement tissues.

Therefore, a filamentous cellular scaffold based on poly (lactide-glycolide) polymer capable of supporting optimal growth of vascular tissue when embedded within a continuous sponge matrix cellular scaffold was synthesized. The use of such a polymer further permits the incorporation of agents, such as polypeptides, nucleic acids or lipids promoting the growth and differentiation of vascular cells therein.

Materials and Methods:

Filaments for a vascular tissue scaffold were prepared from a viscous solution of poly(lactide-glycolide (1:1)) Mw=50,000, in dichloromethane (10-30% w/v) that was spooned into filaments by passing the injected solution into an antisolvent such as methanol or hexanes. The random filaments were slightly compressed so as to form a three dimensional network of filamental bundles that were employed for cell-seeding. Incorporation of a bioactive agent into such a scaffold was effected by mixing the active agent into the polymeric material prior to spooning it into filaments. The active agent can be added as free powdery compound or in a formulated form such as pre-encapsulated in a biodegradable polymeric nano or microspheres. The active agent can also be applied onto the formed filament either by coating the filament with a polymeric solution that contains the active agent which after solvent evaporation forms a thin coating containing the active agent.

Example 3

Paradigms for Growth of Hybrid Tissues Composed of Target Replacement Tissues and their Supporting Vasculature within an Integrated Three-Dimensional Cellular Scaffold Reconstitution of body tissues with tissues grown in three-dimensional artificial cellular scaffolds represents a highly desirable goal for replacement of diseased, defective or absent tissues or organs and is of particular benefit for avoiding rejection of transplanted donor tissues when such reconstitution is not effected with self-tissues. A major obstacle preventing the achievement of this goal is the requirement for vascularization of three-dimensional, biologically-engineered replacement tissues. In order to achieve this desired aim, an artificial cellular scaffold enabling the combined and regulated growth both of target replacement tissues and of their supporting vascular tissues has been constructed. The architecture of such a scaffold is composed of a first filamentous polymeric component designed for the tubular growth of supporting vasculature by endothelial cells which is integrally embedded within a three-dimensional continuous matrix sponge polymer designed to support the growth of the target replacement tissues. Both of these polymeric components were further designed for the regulated delivery of factors promoting specific differentiation of cells desired for each component.

Hence, in order to practice and to enable the full optimization and exploitation of such a tissue replacement method, modalities employing various combinations of ex vivo and in vivo growth of replacement target tissues and their supporting vasculature have been elaborated.

Materials and Methods:

Paradigm for in vivo growth of both target replacement tissues and supporting vascular tissues within an integrated cellular scaffold: In this modality, a filamentous polymer scaffold for growth of vascular cells is integrally embedded within a continuous matrix scaffold for growth of target replacement tissues. This is achieved by inducing polymerization of the continuous matrix polymer scaffold around the filamentous polymer scaffold. The polymers constituting the scaffold were pre-treated so as to optimize the in vivo implantation, growth and/or differentiation of their respective tissues. This was effected by pre-treating the scaffold components to express chemoattractants, adhesion molecules, differentiation factors and/or growth factors and/or to incorporate nucleic acids leading to the production of such factors. This method was further enhanced by the sequential timed-release of these factors so as to recapitulate the natural migration, adhesion, differentiation and/or growth stimuli specific for a given tissue type. For example, to stimulate angiogenesis VEGF was released during early stages of vascular tissue growth and was exchanged with angiopoietins 1, 2 and 3 in sequence as differentiation and vascularization progressed.

Hence, in this tissue replacement therapy modality, an integrated cellular scaffold was implanted in vivo without pre-seeding with precursor cells to promote therein the differential colonization and growth of vascular and target replacement tissues derived from colonizing cells of the recipient (FIG. 2, Paradigm 1).

In vitro growth of supporting vascular tissues within an integrated cellular scaffold combined with in vivo growth of target replacement tissues: Similarly to the method described above, in this modality, the target replacement tissue-specific and the vasculature-specific polymers constituting the scaffold are pre-treated so as to optimize the implantation, growth and/or differentiation of their respective tissues, however in this case the vasculature-specific polymers are pre-treated so as to optimize the in vitro growth of vasculature which is followed by in vivo growth of target replacement tissues (FIG. 2, Paradigm 2). Hence, in this modality, growth of vascular tissues is first performed ex vivo by seeding the scaffold with vascular cells, such as endothelial cells, followed by culturing in a bioreactor under conditions optimal for growth of vascular cells (Vailhe B. et al., Lab Invest. 2001, 81:439) as follows:

Scaffolds are seeded with 2-4 million vascular cells per scaffold by adding a cell suspension in medium of vascular cells on to the scaffold in a 96-well in tubes followed by culturing in spinner flasks or in agitated tubes for 20 hours. These vascular cells can include endothelial cells or pericytes harvested from large blood vessels, skin tissue, foreskin tissue or bone marrow from the patient or from a donor. These pre-seeded angiogenic scaffolds are then further cultured in a bioreactor or in a spinner flask for 7-14 days. Following formation of this angiogenic component, the resulting vascular bed is embedded in the target replacement tissue polymer solution which is induced to polymerize around the vascular infrastructure.

Following this stage, the pre-vascularized scaffold is implanted in a recipient at the desired anatomical location for colonization, growth and differentiation of the target replacement tissue.

Paradigm for ex vivo growth of both target replacement tissues and supporting vascular tissues within an integrated cellular scaffold: In this tissue replacement therapy modality, both the target replacement tissues and the supporting vascular tissues were grown in the integrated cellular scaffold in vitro prior to implantation in vivo (FIG. 2, Paradigm 3). As described in the previous modalities, the target replacement tissue-specific and the vasculature-specific polymers constituting the scaffold were pre-treated so as to optimize the implantation, growth and/or differentiation of their respective tissues, however in this case these were pre-treated so as to optimize their growth and differentiation in vitro prior to implantation in the recipient. Hence, in this modality, the growth of both vascular and target replacement tissues were performed ex vivo by seeding the scaffold with vascular cells and the seeded scaffolds were cultured in a bioreactor under conditions permitting the growth and differentiation of both tissue types as follows:

Filamentous polymer cellular scaffolds were seeded with 2-4 million endothelial cells per scaffold and seeded scaffolds were incubated in spinner flasks or in agitated tubes for 20 hours, following which scaffolds were further incubated in a rotating bioreactor or in a spinner flask for 7-14 days.

Following formation of this angiogenic component, the resulting vascular bed was embedded immersion in a polymerizing continuous matrix polymer solution containing target replacement tissue cells. Alternatively, the integrated cellular scaffold can be seeded with target replacement tissue precursor cells following polymerization by culture in spinner flasks or in agitating tubes for 4-10 hours. Growth of target replacement tissues with the scaffold was effected by culturing the seeded scaffold in a bioreactor for an additional 7 to 14 days.

Following this stage, scaffolds containing reconstituted and vascularized tissues were implanted in recipients at the desired anatomical location in vivo for further colonization and growth of the component tissues.

Example 4

Ectopic Induction of Cartilage Growth In Vivo within a Cellular Scaffold Loaded with DNA Encoding Bone Morphogenetic Protein-2

In order to optimize the homing, adhesion, differentiation and growth of cells within an artificial cellular scaffold it is necessary to create within the scaffold the necessary biological environment to support these processes. This can be achieved by pre-treating the scaffold to display or release polypeptide factors facilitating the homing, adhesion, differentiation and growth of the desired tissue-specific cells. One powerful approach which can be taken to achieve this aim is to incorporate within the scaffold nucleic acids in a form which can be taken up and expressed by cells present within or in close proximity to the scaffold.

In order to achieve this aim, methods were developed employing cellular scaffolds loaded with dextran-complexed or liposome-complexed plasmid to serve as DNA delivery systems.

Figure 3A:
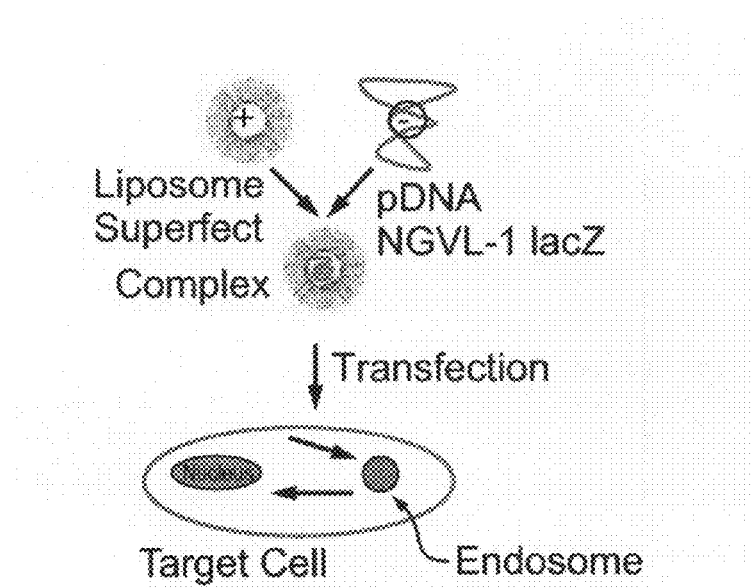
FIGS. 3a-c depicts the genetic modification of a murine mesenchymal stem cell line transfected in vitro with a liposome-complexed plasmid encoding a β-galactosidase marker gene.

Materials and Methods:

In vitro transfection of MSCs with a liposome-complexed plasmid encoding β-galactosidase: MSCs were transfected with a liposome-DNA complex, as depicted in FIG. 3a, to determine the feasibility of this transfection modality prior to performing such a transfection with cellular scaffold loaded liposome-DNA complex. The following describes the protocol for such a transfection in vitro.

Cultured C3H10T1/2 MSCs were transfected with liposome-complexed plasmid pNGVL1-ntbGAL encoding a β-galactosidase marker gene as follows: $1.3 \times 10^5$ cells were cultured in 2 ml complete medium (DMEM supplemented with 2 mM L-glutamine, 100 units/ml penicillin, 100 units/ml streptomycin and 10% FCS) in 6-well plates for 24 hours in a 37° C. humidified incubator with 5% $CO_2$, resulting in growth of a cell monolayer. DNA-liposome complex was prepared by mixing 2.2 ml of 2.2 mM pNGVL1-ntbGAL with 98 ml serum-free medium followed by brief vortexing. To this mixture was added 82 ml of "Superfect" (QUIAGEN) liposome suspension and this mixture was allowed to sit for 5-10 min to allow complexation of plasmid and liposomes after which 486 ml of complete medium was added to the complexation mixture. The cell monolayer was subsequently washed in 1 ml PBS and incubated with liposome-plasmid complex for 2-3 hours.

Efficiency of transfection was determined after 24 h by staining the cultures with X-gal for detection of β-galactosidase expression.

Figure 4A:
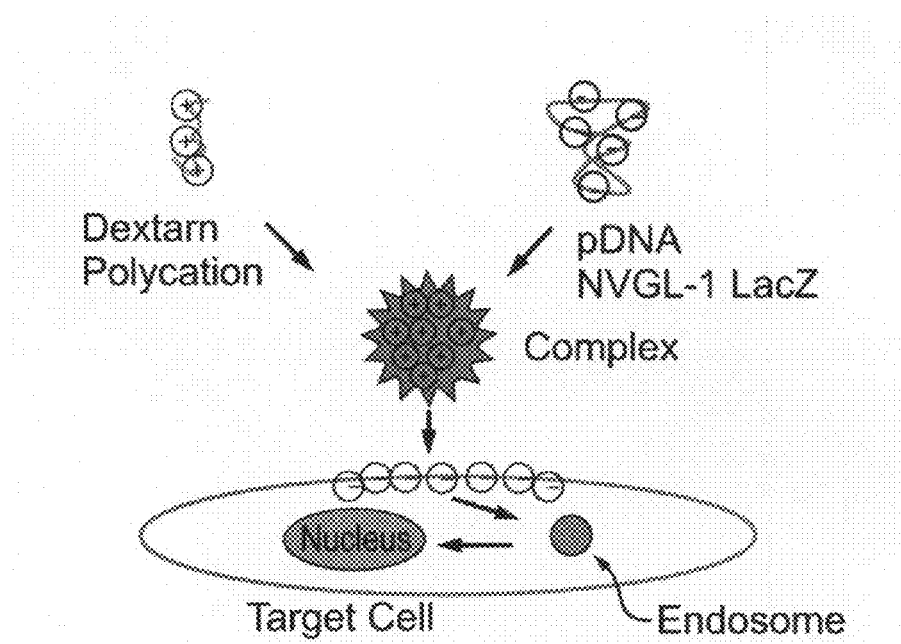
FIGS. 4a-c depicts the genetic modification of a murine mesenchymal stem cell line transfected in vitro with a dextran polycation-complexed plasmid encoding a β-galactosidase marker gene.

In vitro transfection of MSCs using dextran polycation-complexed DNA: Cells of the MSC line C3H10T1/2 were transfected with dextran-complexed plasmid pNGVL1-ntbGAL encoding a β-galactosidase marker gene, as depicted in FIG. 4a, so as to determine the practicality of this transfection modality prior to performing such a transfection with cellular scaffold-loaded dextran-DNA complex. Complexation of DNA to dextran for transfections was performed as follows:

$1.3 \times 10^5$ MSCs cells were cultured in 2 ml complete medium (DMEM supplemented with 2 mM L-glutamine, 100 units/ml penicillin, 100 units/ml streptomycin and 10% FCS) in 6-well plates for 24 hours in a 37° C. humidified incubator with 5% $CO_2$, resulting in growth of a cell monolayer. A transfection mixture consisting of 30 ml of 0.2 mM pNGVL1-ntbGAL, 24 ml dextran polycation and 29 ml HBSS was prepared and allowed to sit for 30 min to allow complexation of DNA and dextran. The cell monolayer was washed with 1 ml of 1×PBS and resuspended in a mixture of 1 ml serum-free medium containing 69 ml of DNA-dextran complex solution. The transfection mixture was incubated for 4 hours in a 37° C. humidified incubator with 5% $CO_2$ and the cells were washed in 1 ml PBS and resuspended in 1 ml complete medium.

Efficiency of transfection was determined after 24 h by staining the cultures with X-gal for detection of β-galactosidase expression.

Preparation of arabinogalactan-chitosan polymeric scaffolds: Arabinogalactan-chitosan scaffolds were loaded with dextran-complexed or liposome-complexed DNA in order to test the ability of such scaffolds to induce cellular colonization and to serve as a DNA delivery system, when loaded with DNA, capable of leading to the up-take and expression of transgenes in colonizing cells.

Arabinogalactan-chitosan cellular scaffolds were prepared as follows:

600 mg chitosan was dissolved in 30 ml 2% acetic acid solution to which 20% (w/w) arabinogalactan was added. Following gel formation, the sample was aliquotted into microtitre plates at 150 ml/well and incubated at 37° C. for 48 hours. Samples were frozen at −80° C., lyophilized and washed with 0.5M NaOH and distilled water until reaching neutral pH. The scaffolds were then re-frozen, lyophilized and sterilized by UV irradiation.

Non-complexed, dextran-complexed and liposome-complexed plasmid was then prepared for incorporation into arabinogalactan-chitosan scaffolds as follows:

DNA-loading of cellular scaffolds: Compositions of plasmid DNA for loading in cellular scaffolds were prepared as follows:

Non-complexed plasmid: 51 ml of 1.5 mM pNGVL1-ntb-GAL was mixed with 49 ml of 5% dextrose Liposome-complexed plasmid: 21 ml of 7.4 mM DOTAP-cholesterol (ROCHE) solution was mixed with 51 ml of 1.5 mM plasmid DNA and 28 ml of 5% dextrose Dextran-complexed plasmid: 27 ml of dextran polymer (4 mg/ml) was mixed with 51 ml plasmid DNA and 22 ml of 5% dextrose Arabinogalactan-chitosan scaffolds were soaked in solutions (described above) containing non-complexed, liposome-complexed or dextran-complexed plasmid and subsequently lyophilized. The soaking and lyophilization steps were repeated until each scaffold accumulated 70 mg of plasmid DNA.

In vivo implantation of scaffolds loaded with β-galactosidase-encoding plasmid compositions: Following demonstration of successful transfection of MSCs (described below) with liposome-complexed and dextran-complexed plasmid pNGVL1-ntbGAL encoding a β-galactosidase marker gene, arabinogalactan-chitosan polymeric cellular scaffolds loaded with non-complexed, dextran-complexed or liposome-complexed pNGVL1-ntbGAL were implanted subcutaneously in mice in order to determine the ability of such plasmid-loaded scaffolds to recruit colonizing cells in vivo and to genetically transform these with the loaded plasmid. Implantation of plasmid-loaded cellular scaffolds and harvesting of samples were performed as follows:

Plasmid-loaded scaffolds were transplanted subcutaneously in C3H/HeN mice and the in vivo-passaged scaffold samples were harvested at two and four weeks post-implantation for analysis of β-galactosidase expression.

In vivo implantation of cellular scaffolds loaded with compositions of plasmid encoding the osteogenic factor BMP-2: Following demonstration of successful expression of a β-galactosidase marker gene in cells colonizing arabinogalactan-chitosan cellular scaffolds loaded with liposome-complexed and dextran-complexed plasmid pNGVL1-ntbGAL encoding a β-galactosidase marker gene (described below), such scaffolds loaded with naked human BMP-2-encoding plasmid pBMP2 were implanted in vivo. This was performed in order to test the ability of such cellular scaffolds loaded with a plasmid encoding a tissue-specific differentiation factor to induce colonization of cells within the scaffold and to genetically modify these with the loaded plasmid.

Implantation of plasmid-loaded cellular scaffolds and harvesting of samples were performed as follows:

Arabinogalactan-chitosan cellular scaffolds were loaded with naked, or liposome-complexed human BMP-2-encoding plasmid. DNA complexation and loading to scaffolds was performed as described above. Scaffolds were processed as described above, with the modification that these were loaded with 200 mg of BMP-2-encoding plasmid DNA per scaffold. Plasmid-loaded cellular scaffolds were then implanted subcutaneously into C3H/HeN and CD Nude mice and, four weeks post-implantation, samples were harvested and processed for histological and immunohistochemical analyses.

Figure 3B:
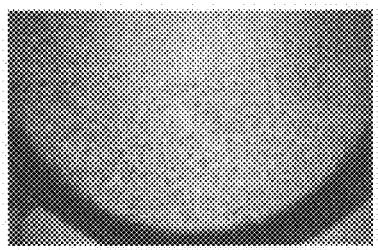
Figure 3C:
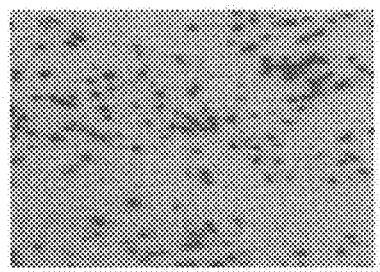

Results:

Efficient in vitro transfection of MSCs with liposome-complexed DNA expression vector: The in vitro efficiency of transfection of MSCs expression with a "Superfect" liposome-DNA (plasmid pNGVL1-ntbGAL encoding a β-galactosidase marker gene) complex was found to be significantly elevated, with 50% of transduced cells displaying production of β-galactosidase, as determined after 24 h by staining cultures with X-gal for detection (FIGS. 3b and 3c).

These results therefore indicate that such loading of cellular scaffolds with liposome-complexed DNA expression vectors can serve as an efficient DNA delivery system for genetically modifying cells colonizing artificial cellular scaffolds.

Figure 4B:
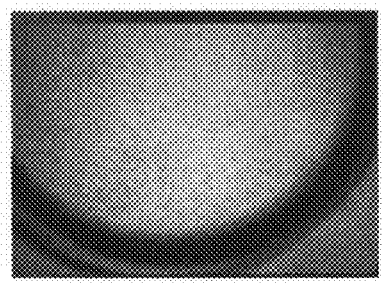
Figure 4C:
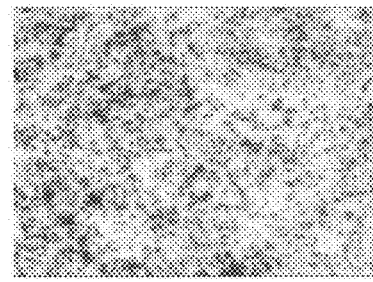

Highly efficient in vitro transfection of MSCs with dextran-complexed DNA expression vector: The in vitro efficiency of transfection of MSCs expression with a dextran polycation-DNA (plasmid pNGVL1-ntbGAL encoding a β-galactosidase marker gene) complex was found to be highly elevated, with 80% of transduced cells displaying production of β-galactosidase, as determined after 24 h by staining cultures with X-gal for detection (FIGS. 4b and 4c).

These results therefore indicate that such loading of cellular scaffolds with dextran-complexed DNA expression vectors can serve as an efficient DNA delivery system for genetically modifying cells colonizing artificial cellular scaffolds in vitro.

Figure 5:
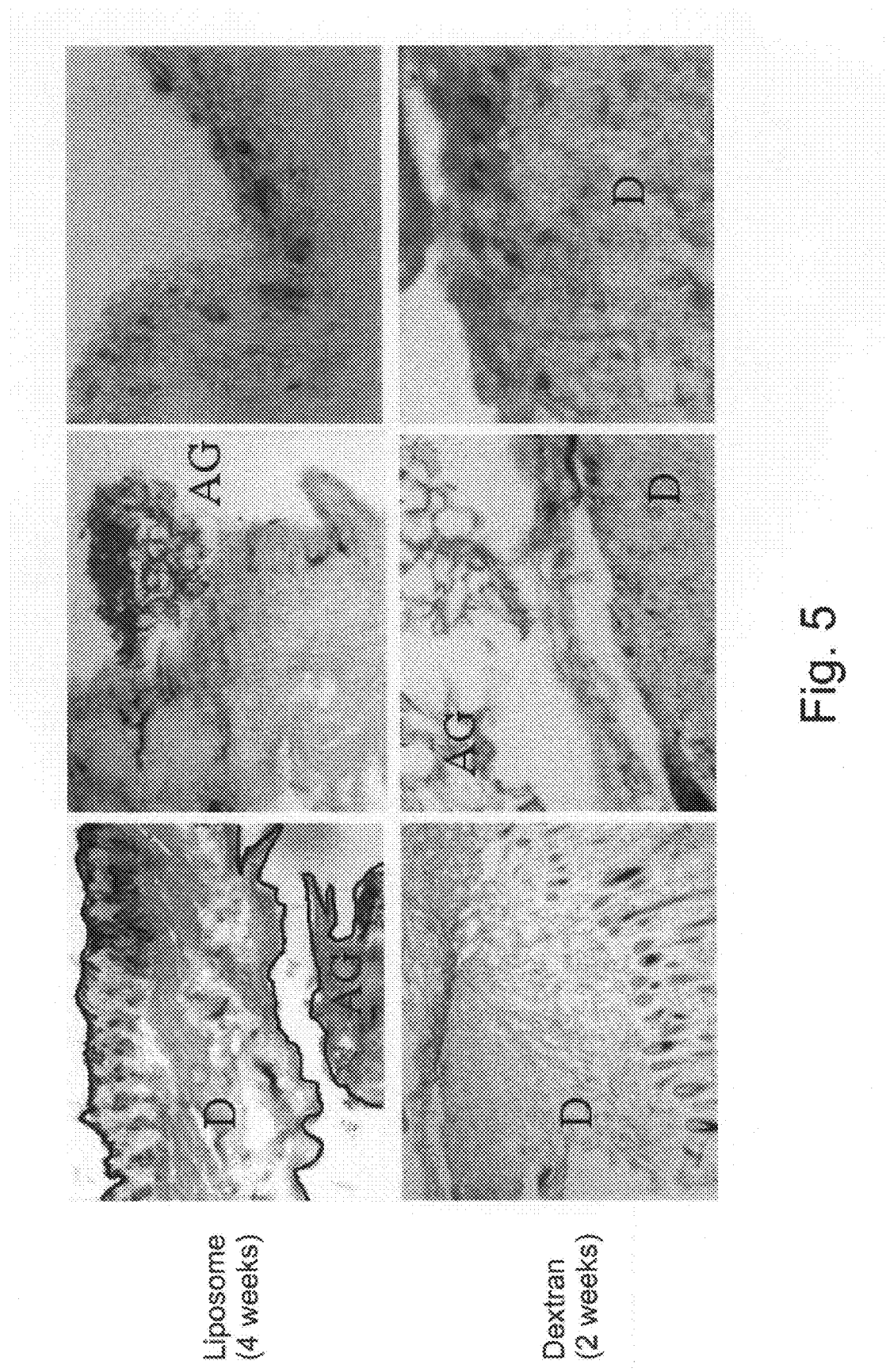
FIG. 5 is a series of photomicrographs depicting the in vivo genetic transformation of mesenchymal stem cells colonizing arabinogalactan-chitosan cellular scaffolds (AG) loaded with liposome-complexed and dextran-complexed plasmid pNGVL1-ntbGAL encoding β-galactosidase. D: dermis.

Efficient in vivo genetic transformation of cells colonizing cellular scaffolds loaded with compositions of a β-galactosidase-encoding plasmid: Arabinogalactan-chitosan cellular scaffolds loaded with liposome-complexed and dextran-complexed plasmid pNGVL1-ntbGAL encoding a galactosidase marker gene passaged in vivo were analyzed for expression of β-galactosidase. Analysis of scaffolds by staining with X-gal detected a significant proportion of β-galactosidase-positive cells in areas adjacent to the liposome- and dextran-plasmid complex-loaded scaffolds at 2 (data not shown) and 4 weeks following implantation (FIG. 5).

Histological analysis of implanted scaffolds furthermore confirmed biodegradation of scaffold polymer in the absence of pathological or adverse immune responses.

These results therefore demonstrate the ability of such liposome- and dextran-plasmid complex-loaded scaffolds to safely serve as in vivo DNA delivery systems capable of genetically modifying cells in the vicinity of implants.

Chondrogenesis is efficiently induced in vivo in implants of cellular scaffolds loaded with compositions of human BMP-2-encoding plasmid: Arabinogalactan-chitosan cellular scaffolds loaded with naked or dextran-complexed human BMP-2 encoding plasmid that had been implanted in vivo were analyzed for growth of cartilage by microscopical analysis. Scaffolds were found to display significant cartilage growth at 4 weeks following implantation (FIG. 6).

These results therefore demonstrate the ability of cellular scaffolds loaded with naked or dextran-complexed BMP-2 encoding plasmid to serve as DNA delivery systems capable of genetically modifying cells in vivo in the vicinity of the implanted cellular scaffold. It was furthermore observed that scaffolds loaded with dextran-complexed plasmid induced higher levels of chondrogenesis as compared to those loaded with naked plasmid DNA.

Example 5

In Vitro Growth of Osteogenic and Vascular Tissues within an Integrated Cellular Scaffold Seeded with MSCs Genetically Modified to Express BMP-2

One strategy for tissue-replacement is to seed and culture cellular scaffolds in vitro with precursor cells specific for the target replacement tissue which have been genetically modified to express a factor promoting the growth and differentiation of such a tissue. Such seeded scaffolds may then be reimplanted in vivo for efficient reconstitution of target replacement tissues.

A major obstacle to tissue replacement effected by in vitro culture of three-dimensional replacement tissues is the requirement for such tissues to be vascularized. As described above, this can be achieved by employing an integrated cellular scaffold containing a filamentous polymer component for growth of vascular cells embedded within a continuous sponge matrix polymer supporting the growth and differentiation of the target replacement tissues. Such an integrated cellular scaffold can thus be seeded with both target replacement tissue precursor cells and vasculogenic cells to thereby form the target replacement tissue with supporting vascularization.

Materials and Methods:

Genetic modification of MSCs to express BMP-2: Murine MSCs genetically modified to express β-galactosidase were further transfected to express the osteogenic factor recombinant human BMP-2. The osteogenic factor BMP-2 was expressed in MSCs in order to stimulate osteogenesis when seeding cellular scaffolds with such cells and the concomitant production of β-galactosidase by these double-transfectants was employed to identify transfectants. BMP-2 was expressed under the regulatory control of tetracycline/doxycycline-inhibited promoter so as to enable the inducible shutting off of BMP-2 expression in the presence of the tetracycline analog doxycycline.

In vitro formation of osteogenic tissue within cellular scaffolds seeded with MSCs genetically modified to express BMP-2: In order to grow bone tissue in vitro, arabinogalactan-chitosan cellular scaffolds were seeded with MSCs genetically modified to express BMP-2. Cellular scaffolds were seeded and cultured as follows:

Arabinogalactan-chitosan scaffolds, prepared as described in Example 4, were hydrated by agitation in 15 ml complete medium for 6 hours. Afterwards, hydrated scaffolds were seeded with $2\times10^6$ MSCs genetically modified to express BMP-2 and β-galactosidase in a volume 1 ml complete medium per scaffold and cultured with agitation at 100 RPM for 20 hours. Seeded scaffolds were then further cultured in a rotating bioreactor (SYNTHECON) at 4 scaffolds per 50 ml vessel for 2 weeks with medium replacement every 48 h.

Formation of osseous tissue was analyzed histologically using masson trichrome to detect collagen I present in osteogenic tissue and alcian blue for detection of chondrocytes.

In vitro culture of arabinogalactan-chitosan cellular scaffolds seeded with endothelial cells and MSCs genetically modified to express BMP-2: One modality for growing target replacement tissues with supporting vasculature within an integrated cellular scaffold conditions is to simultaneously seed an integrated scaffold with cell types giving rise to both the target replacement tissue and supporting vascular tissues and to culture such a seeded scaffold in vitro. However, in order to achieve this, it must be demonstrated that both tissue types can colonize and differentiate within the cellular scaffold together and under the same culture conditions.

Hence, cellular scaffolds were seeded with both endothelial cells and MSCs genetically modified to express BMP-2 and β-galactosidase and were cultured in vitro as follows:

Arabinogalactan-chitosan cellular scaffolds were prepared, hydrated and seeded with genetically modified MSCs together with murine endothelial cell lines β-END-2 or MBA 2.1 as described above using $10^6$ cells each of genetically modified MSCs and endothelial cells per scaffold ($2\times10^2$ total). Seeded scaffolds were cultured in a rotating bioreactor (Synthecon) at 4 scaffolds per 50 ml vessel for 1 week and were then harvested and processed for histological analysis. Frozen 15 mm sections of cultured scaffolds were stained with either H&E or X-gal for detection of cartilage tissue and cells derived from the genetically modified MSCs, respectively.

Figure 7:
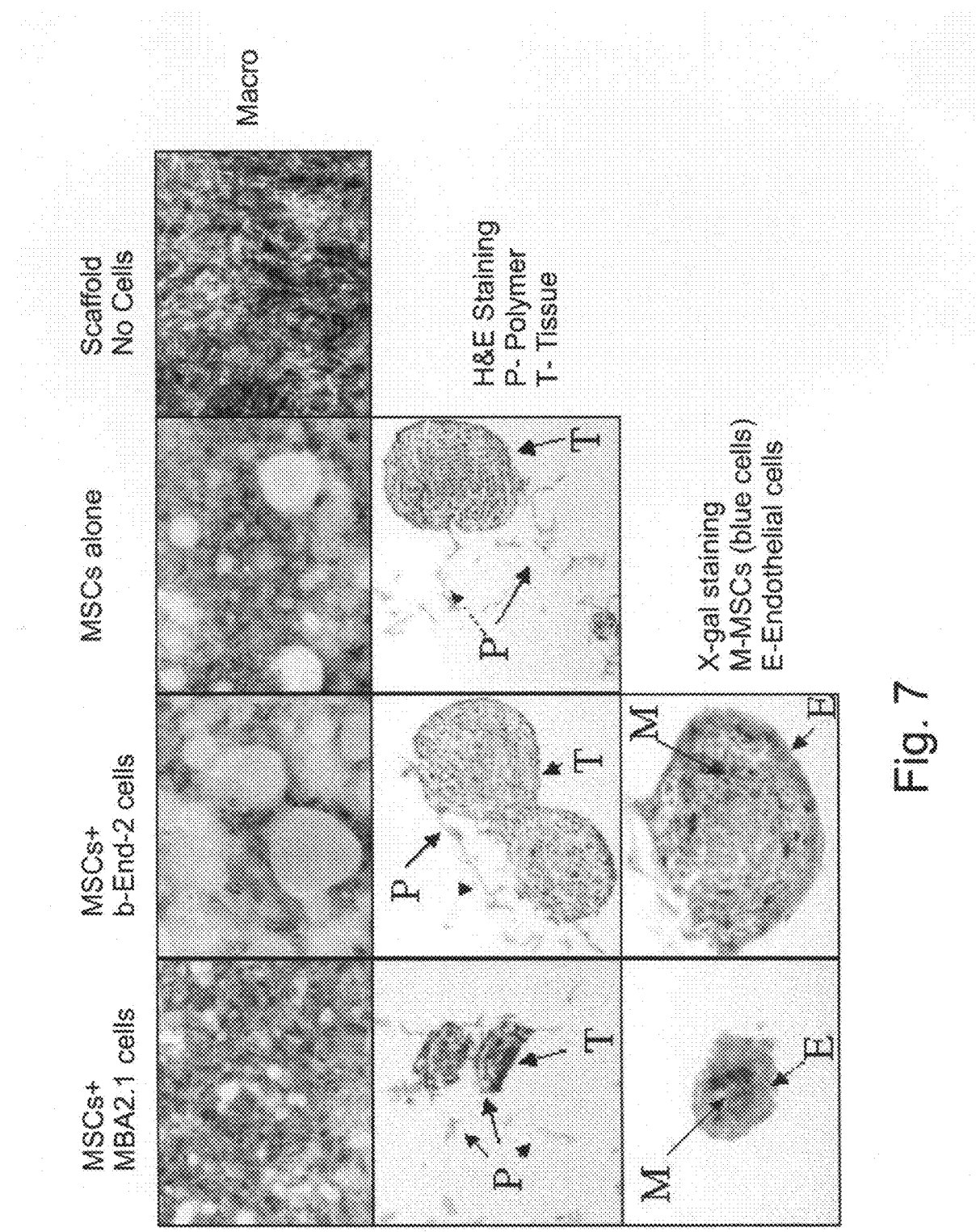
FIG. 7 is a series of photomicrographs depicting in vitro growth of either osseous or combined osseous and vascular tissues in arabinogalactan-chitosan cellular scaffolds seeded with MSCs genetically modified to express either BMP-2 alone or in combination with endothelial cells, respectively.

Results:

In vitro growth of osteogenic tissues in arabinogalactan-chitosan cellular scaffolds seeded with MSCs genetically modified to express BMP-2: Culturing of genetically modified MSCs within arabinogalactan-chitosan cellular scaffolds in a rotating bioreactor for 2 weeks were found to form dense osteogenic tissue displaying bone and cartilage phenotypes, as determined by tissue-specific staining with masson trichrome and alcian blue, respectively (FIG. 7, third column from left).

Thus, these results demonstrate that this system is capable of efficiently generating differentiated cartilage and bone target replacement tissues in vitro by culture of mesenchymal stem cells genetically modified to express BMP-2.

This therefore demonstrates the feasibility of growing tissues in vitro to be utilized in tissue replacement therapy using mesenchymal stem cells genetically modified to express BMP-2 to regenerate osseous tissues.

In Vitro Formation of Hybrid Osteogenic and Vascular Tissues within Cellular Scaffolds Seeded with Endothelial Cells and BMP-2 Expressing MSCs:

Histological analysis of arabinogalactan-chitosan cellular scaffolds seeded with MSCs genetically modified to express BMP-2 and β-galactosidase and cells of either the MBA2.1 or β-END-2 endothelial cell lines revealed formation of hybrid tissue composed of both cell types, as determined by visualization of X-gal-positive and X-gal-negative cells in cultured scaffolds (FIG. 7, first and second columns from left, respectively). The two cell types were furthermore observed to form an organized structure composed of genetically modified MSCs occupying the internal zone of hybrid tissue and endothelial cells lining the outer layers thereof.

These results therefore demonstrate that osteogenic and vasculogenic cells can be cultured ex vivo concomitantly within cellular scaffolds and that under such conditions these cell types can organize themselves to assume their tissue-specific mesenchymal and epithelial architectures, respectively. This indicates therefore that tissue replacement therapy with vascularized in vitro-cultured osseous tissues derived from precursor cells specific to both cell types can be envisaged.

Example 6

In Vivo Growth of Osseous Tissues Derived from MSCs Genetically Modified to Express BMP-2

One strategy for tissue-replacement is to seed cellular scaffolds with precursor cells specific for the target replacement tissue which have been genetically modified to express a factor specific for the growth and/or differentiation of such a tissue. Such seeded scaffolds may then be implanted in vivo in order to reconstitute the target replacement tissue following in vitro culture. This can be achieved by either implanting such scaffolds ectopically, either in the intended recipient or in a donor so as to enable in vivo culturing of replacement tissues. Alternatively, seeded scaffolds can be directly implanted orthotopically within the anatomical location requiring the replacement tissues.

In order to control expression of transgenes in such genetically modified precursor cells a regulatable transgene promoter system can be employed to enable shutting off of transgene expression. This constitutes an important safety feature when implanting genetically modified cells in the context of tissue-replacement therapy.

Materials and Methods:

Ectopic implantation of collagen matrices seeded with MSCs genetically modified to express BMP-2: MSCs were genetically modified to express an osteogenic factor however, in order to determine whether such genetically modified cells can direct the ectopic growth of bone tissue, matrices seeded with these cells were prepared, implanted and analyzed as follows:

Precut collagen sponges (3×3×2 mm, Colastat® #CP-3n, Vitaphore Corp.) were seeded with approximately $10^6$ BMP-2 and β-galactosidase coexpressing MSCs cultured in DMEM supplemented with 2 mM L-glutamine, 100 units/ml penicillin, 100 units/ml streptomycin and 10% FCS. Seeded matrices were then implanted into abdominal muscle of C3H/HEN mice. One control group of mice was maintained with water containing 0.5 mg/ml doxycycline.

Detection of BMP-2 DNA and mRNA in implants was performed, respectively, by PCR and RT-PCR analysis of 1 mg genomic DNA and 2 mg mRNA harvested from abdominal muscle tissues. Transplanted cells were detected immunohistochemically with antibodies recognizing BMP-2 protein.

Orthotopic (bone) implantation of collagen matrices seeded with MSCs genetically modified to express BMP-2: In order to determine whether genetically modified MSCs possessed the capacity to induce the in situ replacement of bone tissue, matrices seeded with these cells were prepared, implanted and analyzed as follows:

Genetically modified MSCs were cultured on Vitrogen collagen gel For 24-48 hours (Vitrogen 100®, Collagen Corporation USA) and cultured gels containing approximately $4×10^4$ cells were implanted into 2.5 mm long segmental gaps created in the radii of ageing (18-20 mo.) osteopenic BALB/c mice.

Bone regeneration was analyzed by micro-CT morphometric analysis 20 days post-implantation.

Results:

Ectopic growth and differentiation of osseous tissues derived from MSCs genetically modified to express BMP-2 implanted in vivo: BMP-2 and β-galactosidase co-expressing MSCs were implanted in abdominal muscle of BALB/c mice were observed to develop into tissues displaying cartilage and bone phenotypes on Day 10 (FIGS. 6a-e,) and to develop into tissues displaying a bone marrow phenotype on Day 20 (FIGS. 6c and e). Genetically modified cells in cartilage tissue and in bone-lining trabecular tissue were found to display chondrocytic and osteoblastic morphologies, respectively, as determined by X-gal staining (FIGS. 6j and 6k, respectively). Immunohistochemical analysis confirmed coexpression of BMP-2 and β-galactosidase in chondrocytes derived from cells genetically modified to express both genes (FIGS. 6l and 6m, respectively) and transcription of BMP-2 mRNA by engrafted cells on Day 20 was confirmed by RT-PCR analysis (FIG. 6o).

In the presence of doxycycline the differentiation of genetically modified MSCs into cells displaying cartilage, bone and bone marrow phenotypes that was observed in the absence of doxycycline, as described above, was shown to be abrogated (FIGS. 8f-i).

These results demonstrated that mesenchymal stem cells genetically modified to express the osteogenic factor BMP-2 are capable of forming organized osseous tissue including cartilage, bone and bone marrow when implanted ectopically in muscle tissue. Such a method can thus be utilized to grow replacement bony tissues ectopically for bone replacement therapy.

Doxycycline-mediated inhibition of BMP-2 mRNA transcription and BMP-2-induced osteogenesis in MSCs genetically modified to express BMP-2 under the regulatory control of a tetracyclineldoxycycline-inhibited promoter: MSCs were genetically modified with a transgene under the regulatory control of a tetracycline-inhibited promoter in order to provide a negative control for expression of BMP-2, thus enabling determination of its effect on differentiation of MSCs and also to provide an inducible shut-off system to terminate expression of a transgene by a genetically modified precursor cell employed in tissue replacement therapy. Doxycycline, a tetracycline analog, was administered in the drinking water of in one control group of animals having received an implant of genetically modified cells.

Figure 8A:
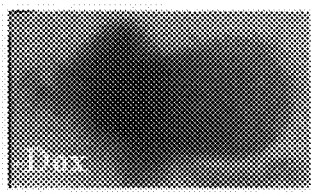
FIGS. 8a-o depict ectopic growth and differentiation of cartilage (C), bone (B) and bone marrow (BM) tissues derived from MSCs genetically modified to express BMP-2 seeded in collagen matrices and implanted in abdominal muscle and depicts doxycycline-mediated inhibition of BMP-2 mRNA transcription and BMP-2-induced osteogenesis by MSCs expressing BMP-2 under the regulatory control of a tetracycline/doxycycline-inhibited promoter.
Figure 8B:
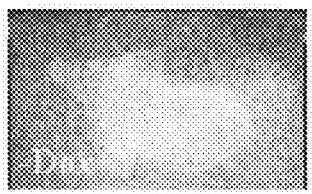
FIGS. 8b and 8g are X-ray photographs depicting growth of calcified tissues in the absence of doxycycline compared with non in the presence of doxycycline, respectively.
Figure 8C:
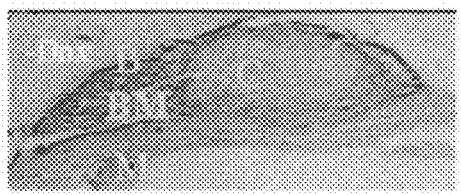
FIGS. 8c and 8h are photomicrographs depicting growth and differentiation of osteogenic tissues composed of cartilage (C), bone (B) and bone marrow (BM) in the muscle tissue (M) in the absence of doxycycline compared with non in the presence of doxycycline, respectively.
Figure 8D:
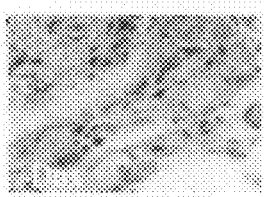
Figure 8E:
Figure 8F:
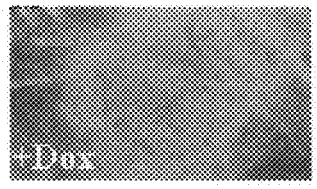
Figure 8G:
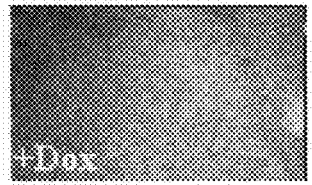
Figure 8H:
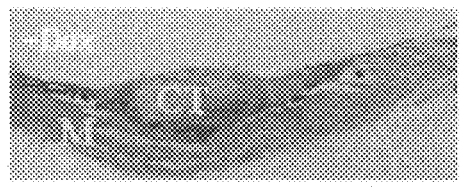
Figure 8I:
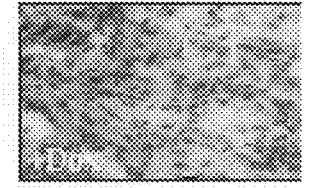
Figure 8J:
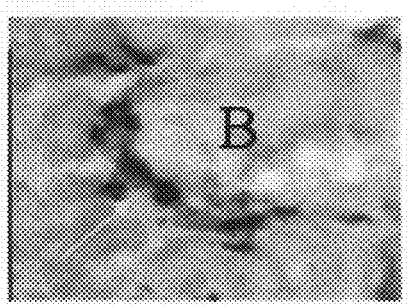
FIGS. 8j and 8k are photomicrographs depicting growth and differentiation of engrafted engineered cells lining trabecular tissue displaying chondrocytic and osteoblastic morphologies, respectively, as determined by X-gal staining, on Day 20.
Figure 8K:
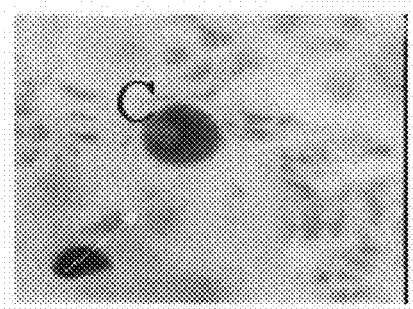
Figure 8L:
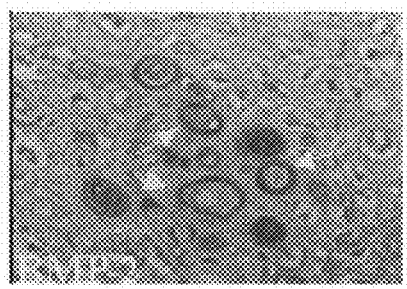
FIGS. 8l and 8m are photomicrographs depicting expression of BMP-2 and β-galactosidase, respectively, in chondrocytes derived from cells genetically modified to express both genes, as determined by immunohistochemical analyses.
Figure 8M:
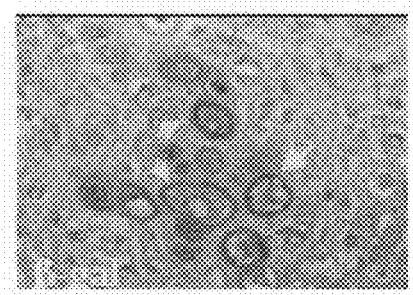
Figure 8O:
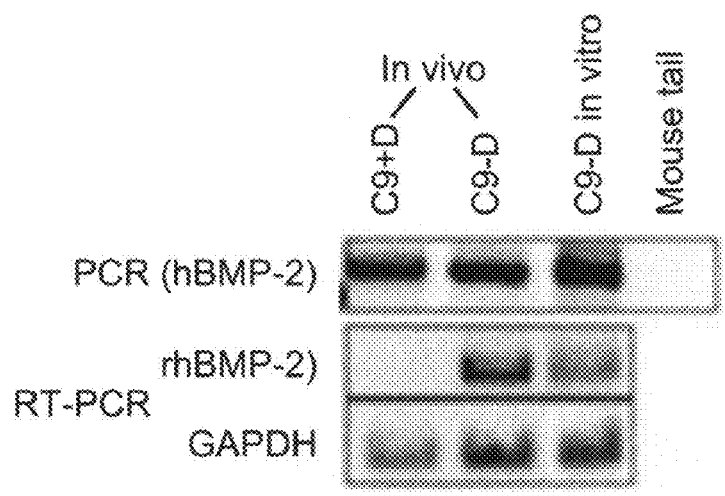

Thus, in the presence of doxycycline, an analog of tetracycline, transcription of BMP-2 mRNA by genetically modified MSCs on Day 20 was shown to be efficiently inhibited, as determined by RT-PCR analysis (FIG. 8o). This provided a rationale for the observation, described above, that differentiation of genetically modified MSCs into osseous tissues in the presence of doxycycline was significantly inhibited.

These results therefore demonstrated that BMP-2 expression was required for efficient differentiation of mesenchymal stem cells into osseous tissues and that the tetracycline-inhibited promoter system employed can serve to efficiently shut off transgene transcription. This provides a vital and highly effective means of controlling transgene expression when employing such genetically modified target replacement tissue precursor cells for tissue replacement therapy.

Figure 9A:
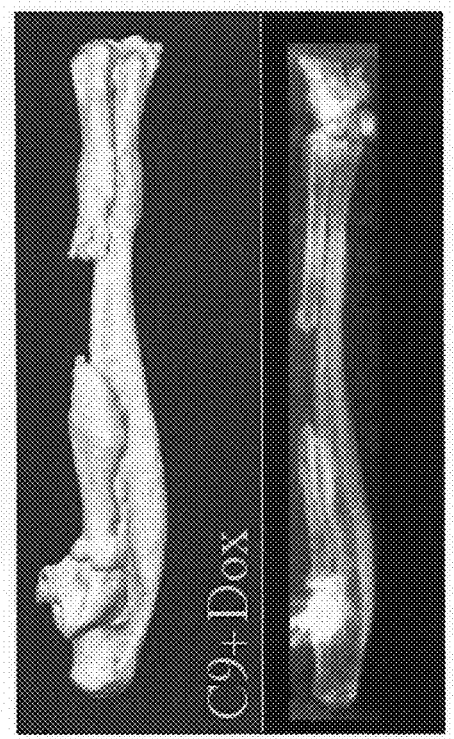
FIGS. 9a and 9b are CT micro-CT imaging data depicting bone regeneration in the absence (−Dox) or presence (+Dox) of doxycycline, respectively.
Figure 9B:
Figure 9C:
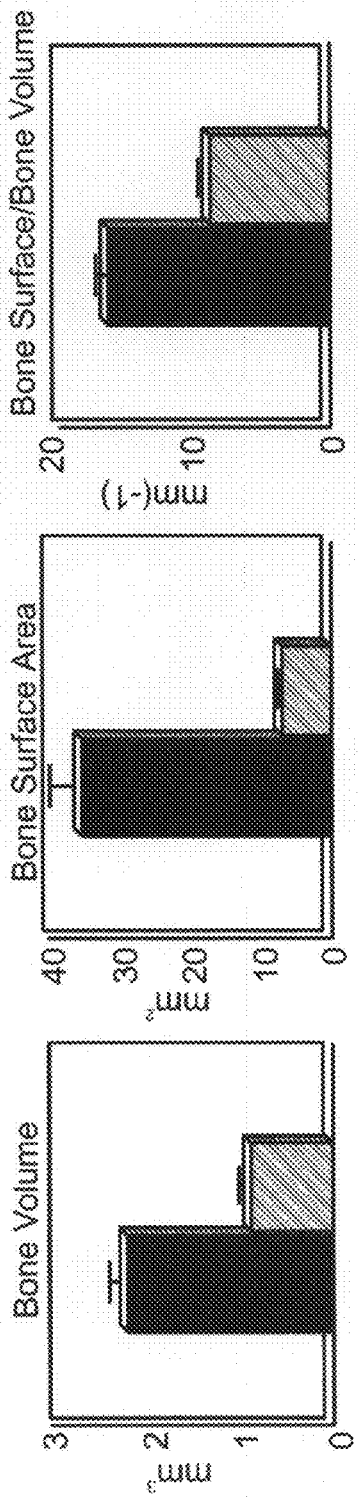
FIG. 9c is a series of morphometric analysis diagrams depicting regenerating bone volume, surface area and surface area to volume ratio in the absence (−Dox) or presence (+Dox) of doxycycline.

Highly efficient orthotopic regeneration of bone tissue in vivo by implantation of collagen matrices seeded with MSCs genetically modified to express BMP-2: Collagen matrices seeded with MSCs coexpressing BMP-2 and under the regulatory control of a tetracycline/doxycycline-inhibited promoter β-galactosidase were shown to have the capacity to regenerate bone when implanted in segmental gaps created in murine radii, as demonstrated via micro-CT morphometric imaging analysis (FIG. 9a). When downregulating BMP-2 expression in the presence of doxycycline (FIG. 9a), bone regeneration was observed to be significantly reduced as measured in terms of regenerated bone volume and surface area which were reduced two and four-fold, respectively (FIG. 9c).

These results indicated, therefore, that mesenchymal stem cells genetically modified to express BMP-2 have the capacity to efficiently regenerate damaged or missing bone tissues in vivo. This demonstrates that bone tissue replacement therapy using such genetically modified precursor cells is feasible. This is consistent with published reports showing that MSCs respond to growth factors to differentiate and give rise to cartilage and bone cells (Triffitt, J T. *Principles of bone biology*. Eds. Bilezikian, J P. et al., Acad. Press Inc. NY. 1996, p. 39).

Example 7

In Vivo Growth of Vascular Tissues within Cellular Scaffolds

A major obstacle to replacement of body tissues with replacement tissues grown within cellular scaffolds is the requirement for such tissues to be vascularized. Vascularization of such cellular scaffold-grown replacement tissues may be induced in vivo by factors promoting angiogenesis, such as factors secreted by the replacement tissue cells themselves, for example, by replacement tissue precursor cells transfected to express such factors. Alternatively, angiogenesis of cellular scaffold-grown replacement tissues can be effected in vivo by pre-seeding of scaffolds with angiogenic cells prior to implantation. An important means of optimizing angiogenesis of replacement tissues grown in cellular scaffolds is to employ scaffolds, as described above, in which a filamentous polymer for the tubular growth of vascular tissues is embedded integrally within a continuous, three dimensional sponge matrix supporting the growth of target replacement tissues.

Materials and Methods:

In vivo implantation of collagen matrices seeded with MSCs genetically modified to express BMP-2 and analysis of vascularization: Vascularization of cellular scaffolds seeded with replacement tissue precursor cells, such as MSCs employed for growing bone tissue, is required for efficient growth of such tissues. Therefore, the ability of the osteogenic factor BMP-2 to promote angiogenesis when produced by MSCs was examined in order to determine the potential of this factor to induce formation of both replacement bone tissue and supporting vasculature. Seeding of cellular scaffolds with such cells, scaffold implantation and assessment of angiogenesis in vivo were performed as follows:

Vitrogen Collagen gels (Vitrogen 100; Collagen Corp., U.S.A.) were seeded with MSCs genetically modified to express the osteogenic factor BMP-2 under the regulatory control of a tetracycline/doxycycline-inhibited promoter and cultured in vitro. Cultured matrices were then implanted subcutaneously in C3H/HeN mice. Twenty days following implantation, implant samples were harvested and analyzed for blood vessel formation by histology and by immunohistochemical staining for detection of the endothelial marker PECAM. The surface area of the blood vessels formed in the implants was quantified via computerized histomorphometry.

Chick chorioallantoic membrane (CAM) angiogenesis assays: In order to determine the angiogenic potential of BMP-2, discs loaded with 25 mg of BMP-2 protein were analyzed by chick CAM assay, as previously described (O'Reilly, M. S. et al. Cell 1994, 79:315).

Analysis of angiogenesis induced in vivo by bone tissue derived in vitro in cellular scaffolds seeded with MSCs genetically modified to express BMP-2: Osteogenic tissue was formed in vitro (see above example 5) from MSCs genetically modified to co-express BMP-2 under the regulatory control of a tetracycline/doxycycline-inhibited promoter and β-galactosidase. Cultured bone tissue was implanted intramuscularly in C3H/HeN mice and, twelve days following implantation, implants were analyzed for angiogenesis and osteogenesis by MRI and histology, respectively.

In vivo growth of vascular tissues within a filamentous cellular scaffold: Optimization of angiogenesis in replacement tissues grown in cellular scaffolds can be achieved by employing a cellular scaffold comprising a filamentous polymer for the tubular growth of vascular tissues around filaments which subsequently biodegrade leaving behind an intact vessel lumen. The in vivo growth of vascular tissues using such a filamentous scaffold was effected as follows:

Filamentous cellular scaffolds, prepared as described in Example 2 were seeded with cells of the B-END-2 endothelial cell line by culturing scaffolds and cells for 20 hours with agitation after which these were transferred a rotating bioreactor for further culturing. Scaffold samples were harvested and processed for analysis of cartilage formation by H&E staining after 3 days of bioreactor culture. After 2 weeks of bioreactor incubation, seeded scaffolds were implanted subcutaneously in CD-nude mice.

Figure 10A:
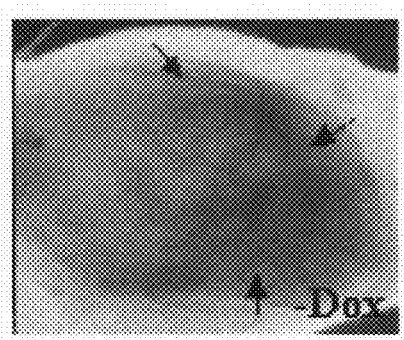
FIGS. 10a and 10c are photomicrographs depicting blood vessel formation in the absence and presence of doxycycline, respectively, in collagen matrix implants seeded with MSCs genetically modified to express BMP-2.
Figure 10B:
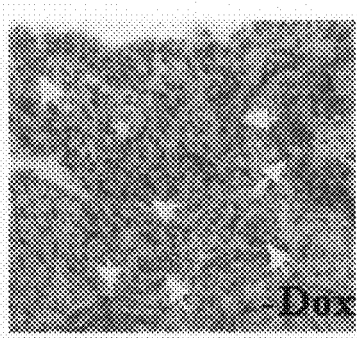
FIGS. 10b and 10d are photomicrographs depicting blood vessel formation, in the absence and presence of doxycycline, respectively, in collagen matrix implants seeded with MSCs genetically modified to express BMP-2, as determined histologically.
Figure 10C:
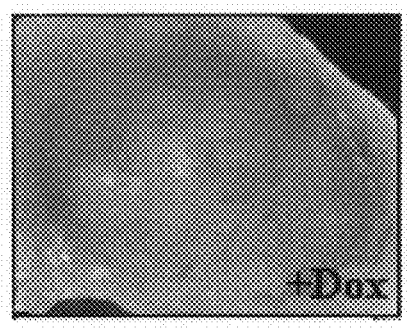
Figure 10D:
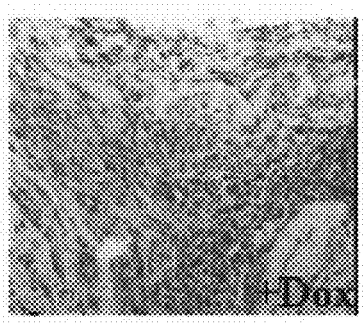
Figure 10E:
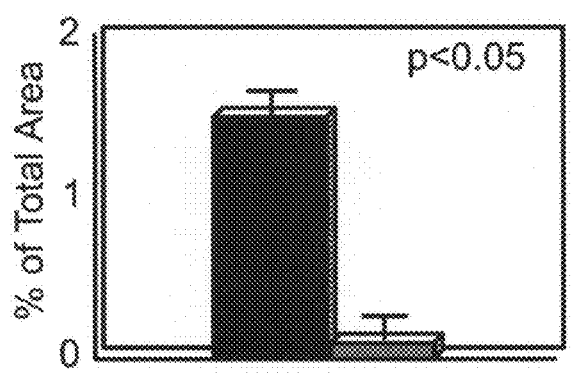
FIG. 10e is a diagram depicting blood vessel formation, in the absence or presence of doxycycline in collagen matrix implants seeded with MSCs genetically modified to express BMP-2 (C9), as determined by morphometric analysis of blood vessel surface area.

Results:

In vivo vascularization induced by MSCs genetically modified to express BMP-2 seeded in collagen matrix implants: Twenty day-old intra-muscular implants of collagen matrices seeded with MSCs genetically modified to express BMP-2 exhibited increased blood vessel formation compared to such implants maintained under conditions preventing expression of BMP-2, as determined by microscopic analysis (FIGS. 10a and 10c, respectively), histological analysis (FIGS. 10b and d, respectively). Scaffold were also shown to display significant angiogenesis by immunohistochemical staining of the endothelial marker PECAM (FIG. 10f) and via computerized histomorphometry (FIG. 10e). Furthermore, formation of vascularized ectopic bone and cartilage ossicle were observed In transplants of MSCs deprived of doxycycline treatment (FIG. 10f).

These results therefore indicate that BMP-2 expressed by MSCs induces angiogenesis and that MSCs genetically modified to express BMP-2 can induce both osteogenesis and supporting angiogenesis when implanted within a scaffold in vivo for bone tissue replacement therapy.

Figure 10G:
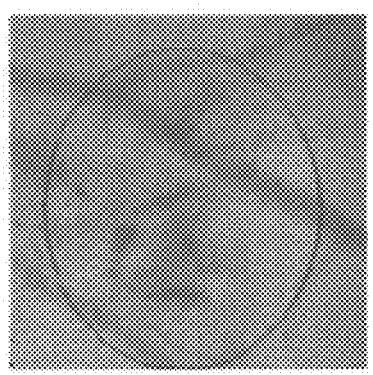

Angiogenesis induced by 10 mg BMP-2 in chick CAM assays: A chick CAM assay of angiogenesis induced by BMP-2 clearly indicated that this protein has an angiogenic effect at a quantity of 10 mg comparted to non in vehicle injection (FIGS. 10g and 10h respectively) providing further support for the observation that this factor is angiogenic and can be employed to generate both bone tissue and supporting vasculature when implanted within a scaffold in vivo for bone tissue replacement therapy.

Figure 16A:
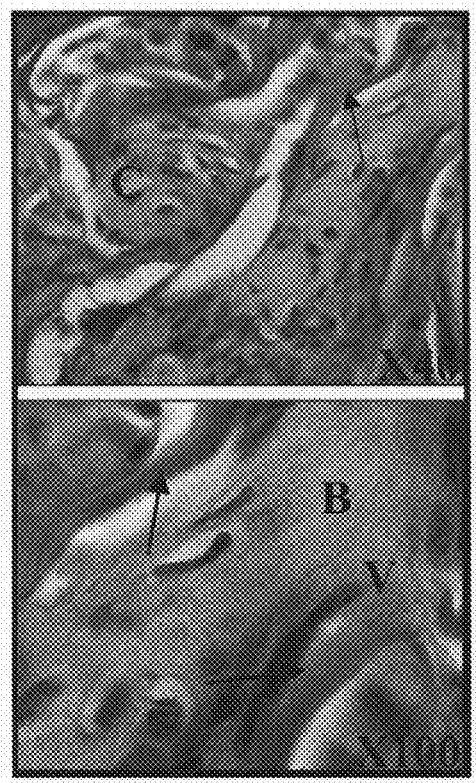
FIGS. 16a-c illustrate tissue sections taken from cell seeded scaffolds implanted in immune deficient mice (CD-1 nude mice) for six weeks. The tissue sections were stained with Hematoxiline & Eosin (FIGS. 16a and c), and Masson's Trichrome (FIG. 16b). The staining clearly demonstrates the formation of bone trabecules within the implant.
Figure 16B:
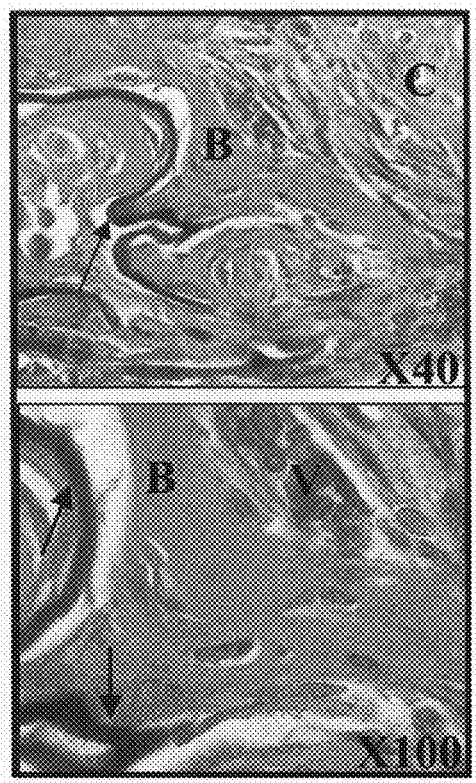
Figure 16C:
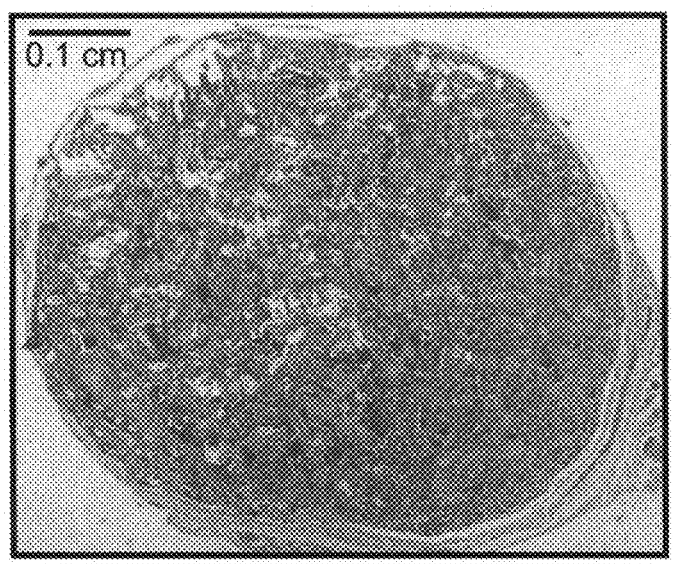
Figure 17A:
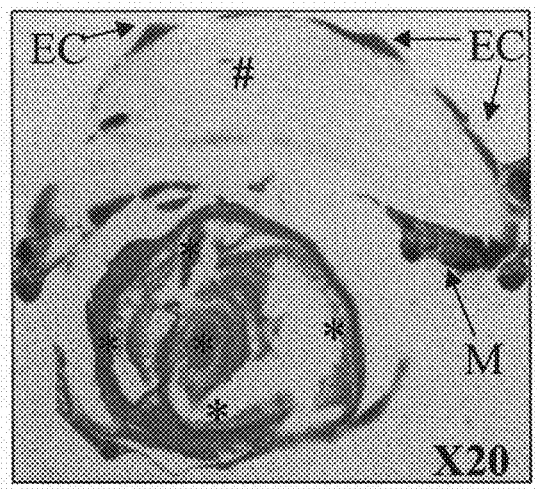
FIGS. 17a-f illustrate scaffolds seeded with genetically engineered AMSCs (C9 cells) conditionally expressing rhBMP2 under tet regulation. The cells were grown in static culture conditions till confluency. The cells were then mixed with arabinogalactan-chitosan beads and cultured in rotary bioreactor for one week. In parallel, 2×106 B-END-2 cells (endothelial cell-line) were seeded on PLA filaments and cultured in a different vessel of the rotary bioreactor for one week. The arabinogalactan beads and the PLA filaments were then co-cultured in a single vessel of the rotary bioreactor and were allowed to form a hybrid structure (FIG. 17e-f). Since the C9 cells were engineered to express the marker gene LACZ and the B-END-2 cells were engineered the marker gene GFP, it was possible to demonstrate the spatial relations between the two cell types (FIGS. 17a-d). M: AMSCs; EC: b-End-2 Endothelial Cells; #: Filament-like polymeric scaffold; Asterisks: Micro-beads scaffold.
Figure 17B:
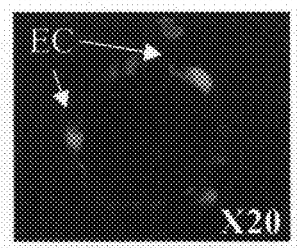
Figure 17C:
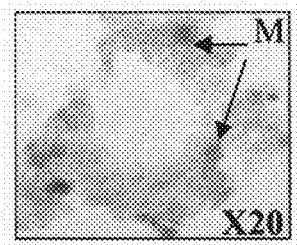
Figure 17D:
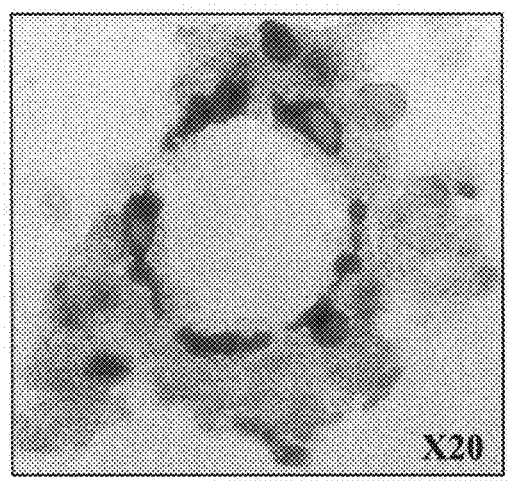
Figure 17E:
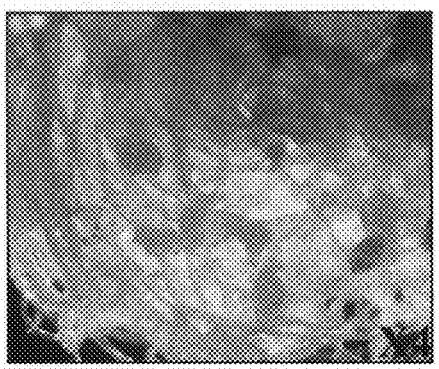
Figure 17F:
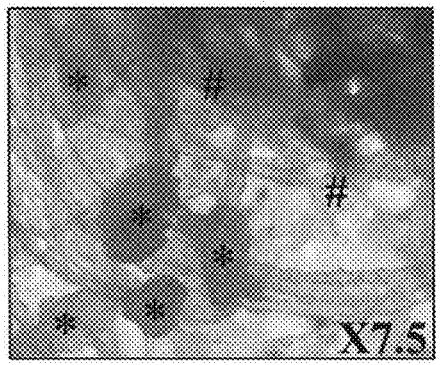

Angiogenesis and chondrogenesis induced in vivo by osseous tissue formed by culturing cellular scaffolds seeded with MSCs genetically modified to express BMP-2: Intramuscular implants of osseous tissue formed in vitro by seeding cellular scaffolds with MSCs genetically modified to express BMP-2 were shown to engraft and to undergo very high levels of vascularization on Day 12, as evidenced by the numerous blood vessels visualized by microscopy and by MRI (FIGS. 11a and 11b, respectively). Histological analysis of H&E stained frozen sections furthermore demonstrated significant growth of cartilage in the transplant area (FIG. 16a,c).

These results therefore demonstrate that bone tissue replacement therapy utilizing implants of osseous tissue formed in vitro by seeding cellular scaffolds with MSCs genetically modified to express BMP-2 generates replacement bone tissues which become highly vascularized in vivo. The capacity to induce such vascularization is critical for optimal engraftment of cellular scaffold-grown tissue replacement grafts.

Formation of vascular tissue in vivo in implants of filamentous cellular scaffolds cultured in vitro with endothelial cells: Following 6 days of bioreactor incubation of filamentous cellular scaffolds seeded with cells of the BP-END-2 endothelial cell line, the endothelial cells were shown to cover the scaffold filaments as demonstrated by H&E staining of frozen sections (FIG. 12).

Figure 13A:
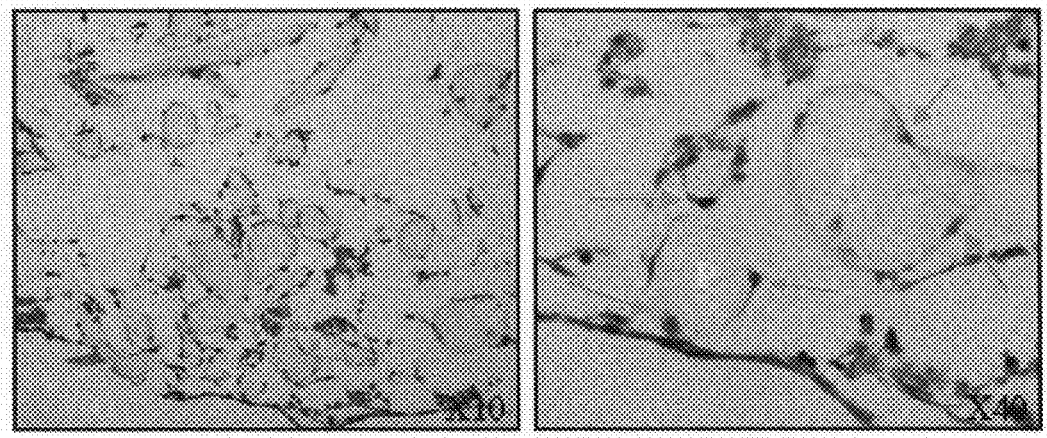
FIGS. 13a-b depicts vascularization of in vivo implants of filamentous cellular scaffolds cultured in vitro with endothelial cells.
Figure 13B:
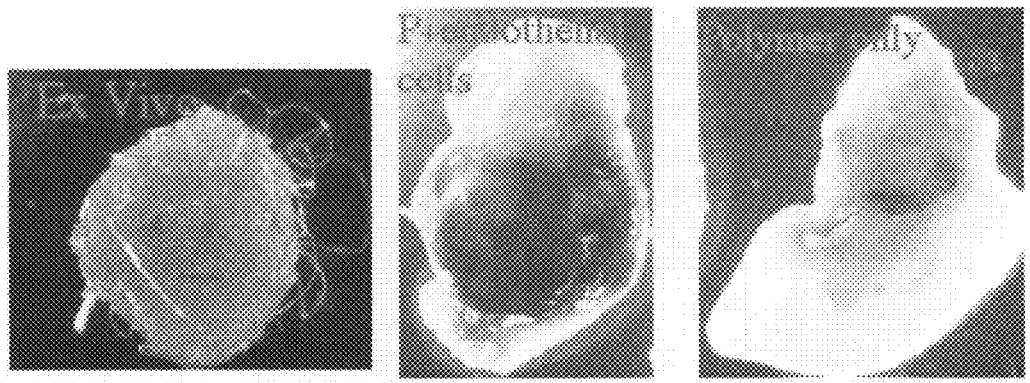
Figure 14A:
FIGS. 14a-g illustrate staining and RT-PCR analysis of genetically engineered AMSCs (C9 cells) conditionally expressing rhBMP2 under tet regulation. The cells were grown under static culture conditions till confluency and then seeded on arabinogalactan-chitosan scaffolds in 96 well-plate (2×106 cells/scaffold; each scaffold: 5 mm in diameter and 2-3 mm in width) for 24 hours. The scaffolds were placed in a rotary bioreactor (4 scaffolds per 50 ml vessel). The vessels were rotated at 15 to 18 RPM. Half of the medium volume was changed every other day for 5 weeks and osteogenic supplements were added (10 mM □glycerophosphate and 50 ug/ml Ascorbic acid).
Figure 14B:
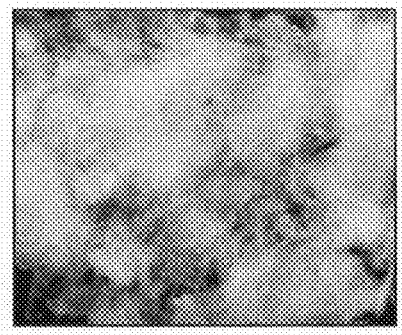
Figure 14C:
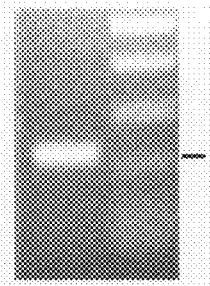
Figure 14D:
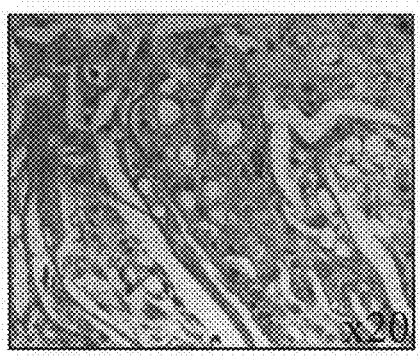
Figure 14E:
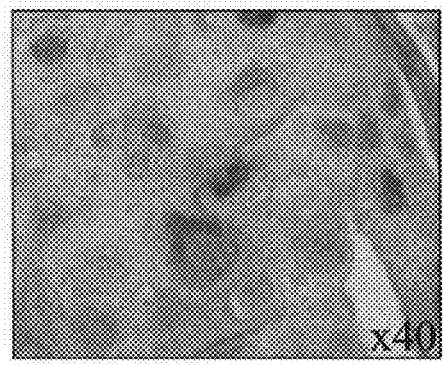
Figure 14F:
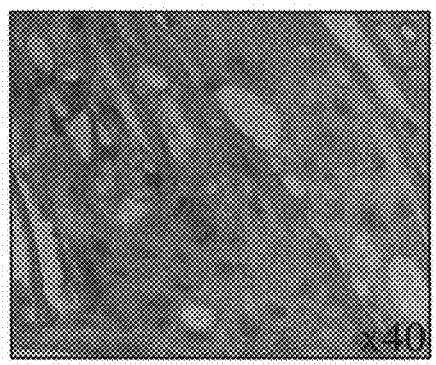
Figure 14G:
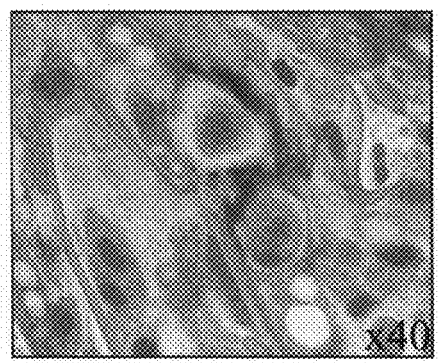
Figure 15A:
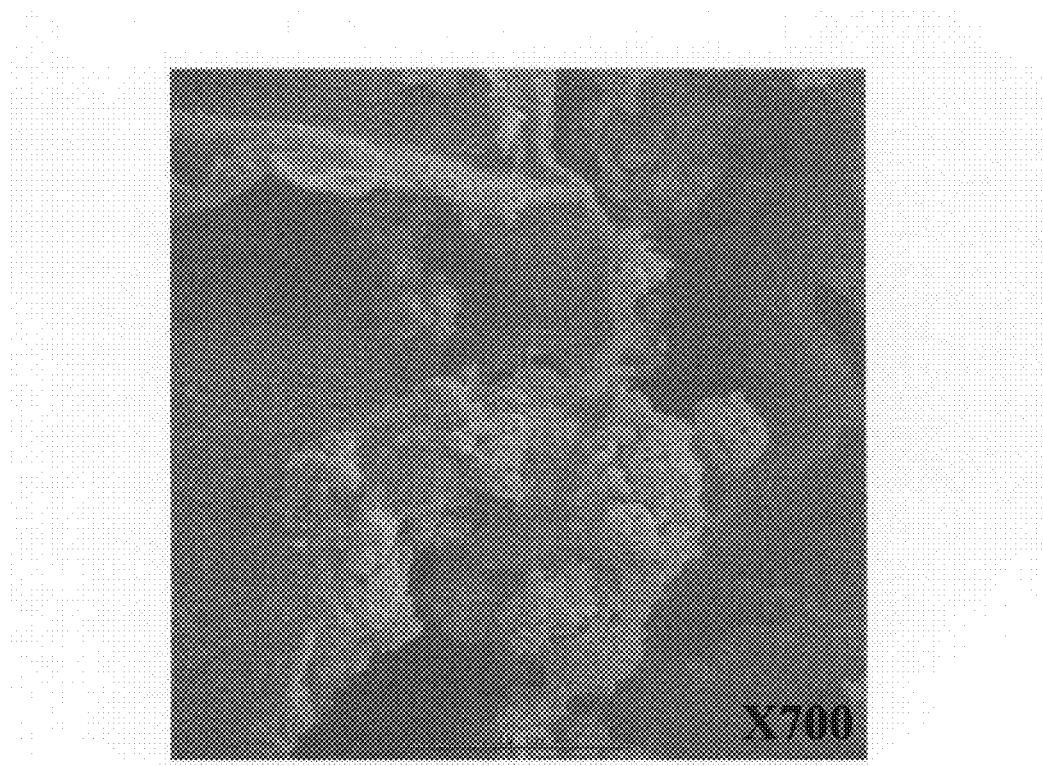
FIGS. 15a-b illustrate a scanning electron micrograph (FIG. 15a) and a computerized regeneration (FIG. 15b) of genetically engineered AMSCs (C9 cells) which were grown as described in FIG. 14 for 30 days.
Figure 15B:
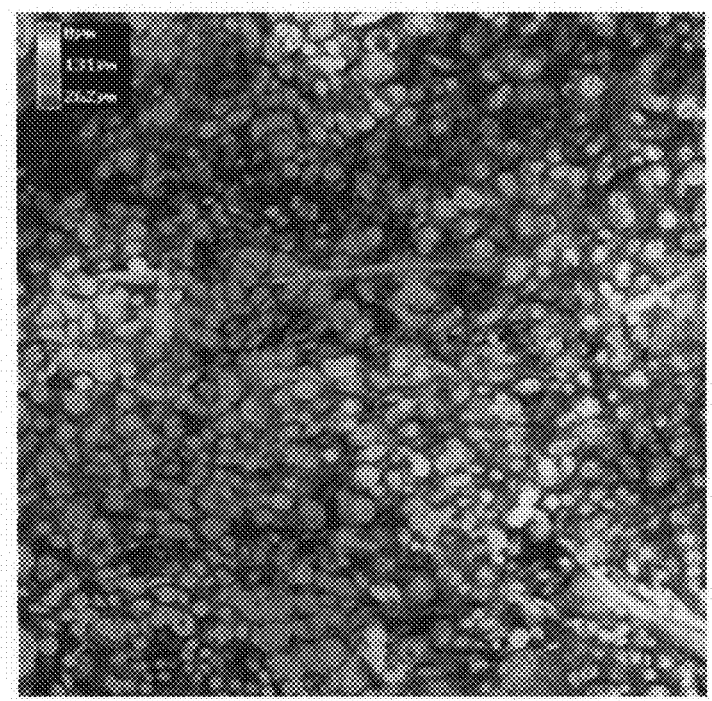

Following two weeks of subcutaneous implantation (which followed two weeks of bioreactor incubation), filamentous cellular scaffolds seeded with cells of the B-END-2 endothelial cell line displayed massive vascularization (FIG. 13). These results thus show that the seeding of such filamentous cellular scaffolds with endothelial cells represents a highly efficient technique to generate vasculature which can be employed either to regenerate vascular tissues in vascular tissue replacement therapy or to provide supporting vasculature in target tissue replacement therapy, thus greatly optimizing engraftment of such cellular scaffold-grown replacement tissues.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES

Additional References are Cited in the Text

Cohn, N A, Kim, B S, Mooney, D J, Emelianov, S Y and O'Donnel, M. (1997) Layer imaging in tissue engineering an using elasticity microscope. Proc. IEEEE Ultrasonic Symp., pp. 1431-1434.

Colton, C K. (1995) Implantable biohybrid artificial organs. Cell Transplant.

Garnet, C, Larche, N, vico, L, Alexandre, C, Lafage-Proust, M H. (1998) Rotating-wall vessels, promising bioreactors for osteoblastic cell culture: comparison with other 3D conditions. Cell Egn, 3, 513-519

Hadlock, T, Singh, S, Vacanti, J P, MacLaughlin, B J. (1999) Ocular cell monolayers cultured on biodegradable substrates. Tissue Eng, 5, 187-196

Kale, S, Biermann, S, Edwards, C, Tarnowski, C; Morris, M, Long, M W. (2000) Three-dimentional cellular development is essential for ex vivo formation of human bone. Nature Biotechnology, 18, 954-958

Kang, H W, Tabata, Y, Ikada, Y. (1999) Fabrication of porous gelatin scaffolds for tissue engineering. Biomaterials, 20, 1339-1344

Kawase, M, Michibayashi, N, Nakashima, Y, Kurikawa, N, Yagi, K, Mizoguchi, T. (1997) Application of gutaraldehyde-cross-linked chitosan as a scaffold for hepatocyte attachment. Biol Pharm Bull, 20, 708-710

Klement, B J, Spooner, B S. (1993) Utilization of microgravity bioreactors for differentiation of mammalian skeletal tissue. J Cell Biochem, 51, 252-256

Madihally, S V, Matthew, H W T. (1999) Porous chitosan scaffolds for tissue engineering. Biomaterials, 20, 1133-1142

Martin, I, Padera, R F, Vunjak-Novakovic, G, Freed, L E. (1998) Ex vivo differentiation of chick embryo bone marrow stromal cells into cartilagenous and bone-like tissues. J Ortho Res, 16, 181-189

Matsuura, T, Kawada, M, Hasumura, S, Nagamori, S, Obata, T, Yamaguchi, M, Hataba, Y, Tanaka, H, Shimizu, H, Unemura, Y, Nonaka, K, Iwaki, T, Kojima, S, Aizaki, H, Mizutani, S, Ikenaga, H. (1998) High-density culture of immortalized liver endothelial cells in the radial-flow bioreactor in the development of an artificial liver. Int J Artif Organs, 21, 229-234

Mooney, D J, Sano, K, Kaufmann, P M, Majahod, K, Schloo, B, Vacanti, L P and Langer, R. (1997) Long term engrfatment of hepatocytes transplanted on biodegradable polymer sponges. J Biomed Mater Res, 37, 413-420

Natsume, T, Ike, O, Okada, T, Takimoto, N, Shimizu, Y, Ikada, Y. (1993) Porous collagen sponge for esophageal replacement. J Biomed Mater Res, 27, 867-875

Niklason, L E, Gao, J, Abbott, W M, Hirschi, K K, Houser, S, Marini, R, Langer, R. (1999) Functional arteries grown ex vivo. Science, 16, 489-493

O'Reilly, M. S. et al. (1994) Angiostatin: a novel angiogenesis inhibitor that mediates the suppression of metastases by Lewis lung carcinoma. Cell. 79, 315-328.

Pollok, J M, Kluth, D, Cusick, R A, Lee, H, Utsunomiya, H, Ma, P X, Langer, R, Broelsch, C E, Vacanti, J P. (1998) Formation of spheroidal aggregates of hepatocytes on biodegradable polymers under continuous-flow bioreactor conditions. Eur J Pediatr Surg, 8, 195-199

Qiu, Q Q, ducheyne, P, Ayyaswamy, P S. (1999) Fabrication, characterization and evaluation of bioceramic hollow microspheres used as microcarriers for 3-D bone tissue formation in rotating bioreactors. Biomaterials, 20, 989-1001

Shand, J M, Haggie A A C. (2000) Use of a resorbable fixation system in orthognathic surgeryP British Journal of Oral and Maxillofacial Surgery 38, 335-337

Shapiro, L, Cohen, S. (1997) Novel alginate sponges for cell culture and transplantation. Biomaterials, 18, 583-590

Shea, L D, Smiley, E, Bonadio, J, Mooney, D J. (1999) DNA delivery from polymer matrices for tissue engineering. Nature Biotechnology, 17, 551-555

Shea, L D, Wang, D, Franceschi, R T, Mooney, D J. (2000) Engineered bone development from a pre-osteoblast cell line on three-dimensional scaffolds. Tissue Eng, 6, 605-617

Triffitt, J T. The stem cell of the osteoblast. Chapter 4 In Principles of bone biology. Editors: JP Bilezikian, L G Raisz and GA Rodan. Academic Press Inc. New York. 1996. Pp. 39-50.

Voigt, M, Schauner, M, Scaefer, D J, Andree, C, Horch, R, Stark, G B. (1999) Cultured epidermal keratinocytes on a microspherical transport system are feasible to reconstitute the epidermis in full-thickness wounds. Tissue Eng, 5, 563-572

Yagi, K, Michibayashi, N, Kurikawa, N, Nakashima, Y, Mizoguchi, T, Harada, A, Higashiyama, S, Muranaka, H, Kawase, M. (1997) Effectiveness of fructose-modified chitosan as a scaffold for hepatocyte attachment. Biol Pharm Bull, 20, 1290-1294

What is claimed is:

1. A method of forming a heterogeneous tissue, the method comprising: (a) growing vascular cells on a filamentous scaffold so as to form tubular vascular structures thereupon; (b) embedding said filamentous scaffold comprising said tubular vascular structures in a porous continuous scaffold thereby forming a composite scaffold; (c) contacting said composite scaffold with cells of a non-vascular tissue type; and (d) growing said vascular cells and said cells of a non-vascular type in said composite scaffold, thereby forming said heterogenous tissue.

2. The method of claim 1, wherein said contacting is effected by ex-vivo seeding said cells of a non-vascular tissue type on said composite scaffold.

3. The method of claim 1, wherein said contacting is effected by implanting said composite scaffold in a subject.

4. The method of claim 1, wherein said vascular cells are endothelial cells or pericytes.

5. The method of claim 1, wherein said filamentous scaffold has a diameter not exceeding 0.5 mm.

6. The method of claim 1, wherein said vascular cells are from large blood vessels, skin tissue, foreskin tissue or bone marrow.

7. The method of claim 1, wherein said non-vascular tissue cells are structural tissue cells selected from the group consisting of bone forming and muscle forming cells.

8. The method of claim 1, wherein said composite scaffold comprises a plurality of molecules of a polymeric backbone cross-linked there between via L and D stereoisomers of a linker molecule.

9. The method of claim 1, wherein said non-vascular tissue type is structural tissue selected from the group consisting of bone tissue, cartilage tissue, adipose tissue, connective tissue and muscle tissue.

10. The method of claim 1, wherein said filamentous scaffold or said porous continuous scaffold or both further include a bioactive agent associated therewith.

11. The method of claim 10, wherein said bioactive agent is selected from the group consisting of a cell proliferation factor, a cell differentiation factor, a cell attracting factor and a pharmacologically active factor.

12. The method of claim 1, further comprising growing said non-vascular tissue type on said porous continuous scaffold prior to step (c).

13. The method of claim 1, wherein said filamentous scaffold or said porous continuous scaffold or both are degradable upon exposure to predetermined environmental conditions.

14. The method of claim 13, wherein said predetermined environmental conditions are selected from the group consisting of presence of hydrolytic enzymes, presence of proteasomal enzymes, pH lower than 5 and reducing conditions.

15. The method of claim 8, wherein said linker molecule is a co-polymer of lactic acid.

16. The method of claim 8, wherein said polymer backbone is a hydrophilic polymer.

17. The method of claim 16, wherein said hydrophilic polymer is selected from the group consisting of a natural polysaccharide, a protein, an ethylene glycol based polymer and a propylene glycol based polymer.

18. The method of claim 1, wherein the structure of said filamentous scaffold or said porous continuous scaffold or both is three dimensional.

* * * * *